(12) United States Patent
Bendahan et al.

(10) Patent No.: US 9,625,606 B2
(45) Date of Patent: Apr. 18, 2017

(54) SYSTEMS AND METHODS FOR HIGH-Z THREAT ALARM RESOLUTION

(71) Applicant: Rapiscan Systems, Inc., Torrance, CA (US)

(72) Inventors: Joseph Bendahan, San Jose, CA (US); Edward James Morton, Guildford (GB); David Yaish, Tel Aviv (IL); Yossi Kolkovich, Tel Aviv (IL); Jacques Goldberg, Haifa (IL)

(73) Assignee: Rapiscan Systems, Inc., Torrance, CA (US)

( * ) Notice: Subject to any disclaimer, the term of this patent is extended or adjusted under 35 U.S.C. 154(b) by 0 days.

(21) Appl. No.: 15/015,369

(22) Filed: Feb. 4, 2016

(65) Prior Publication Data

US 2016/0216398 A1 Jul. 28, 2016

Related U.S. Application Data

(63) Continuation of application No. 14/516,146, filed on Oct. 16, 2014, now Pat. No. 9,310,323.
(Continued)

(51) Int. Cl.
*G01J 5/00* (2006.01)
*G01V 5/00* (2006.01)

(52) U.S. Cl.
CPC ................. *G01V 5/0016* (2013.01)

(58) Field of Classification Search
CPC ..... G01T 1/2935; G01T 1/185; G01V 5/0091; H01J 27/02
See application file for complete search history.

(56) References Cited

U.S. PATENT DOCUMENTS 2,003,120 A 5/1935 Penniman
2,004,116 A 6/1935 Hollis
(Continued)

FOREIGN PATENT DOCUMENTS

CA 2624658 A1 9/2009
CA 2624663 A1 9/2009
(Continued)

OTHER PUBLICATIONS

International Search Report for PCT/GB2009/001275, Jul. 24, 2009, Rapiscan Security Products Inc.
(Continued)

*Primary Examiner* — Kiho Kim
(74) *Attorney, Agent, or Firm* — Novel IP

(57) ABSTRACT

A second stage screening system configured to resolve a threat alarm detected in a cargo by a first stage screening system. The second stage screening system includes layers of first muon detectors placed above the cargo to detect a first coordinate and an angle of incidence of incoming muons and layers of second muon detectors placed below the cargo to detect an actual coordinate and an actual angle of exit of the incoming muons. The first and second detectors measure a momentum of the incoming muons. A processing unit receives threat sensitivity vectors determined from the first stage, operates a cargo positioning system that centers a high-Z threat within the cargo, relative to the first and second muon detectors, and analyzes the momentum and a distribution of deflection angles between the angles of incidence and exit to resolve the threat alarm.

20 Claims, 13 Drawing Sheets

Related U.S. Application Data

(60) Provisional application No. 61/891,886, filed on Oct. 16, 2013.

(56) References Cited

U.S. PATENT DOCUMENTS

| | | |
|---|---|---|
| 2,007,120 A | 7/1935 | Holmes |
| 2,008,221 A | 7/1935 | Molander |
| 2,299,251 A | 10/1942 | Perbal |
| 2,831,123 A | 4/1958 | Daly |
| 2,971,433 A | 2/1961 | Akin |
| 3,140,397 A | 7/1964 | Henry |
| 3,374,355 A | 3/1968 | Parratt |
| 3,603,793 A | 9/1971 | Warren |
| 3,676,783 A | 7/1972 | Kinbara |
| 3,707,672 A | 12/1972 | Miller |
| 3,713,156 A | 1/1973 | Pothier |
| 3,766,387 A | 10/1973 | Heffan |
| 3,767,850 A | 10/1973 | McMillian |
| 3,770,955 A | 11/1973 | Tomita |
| 3,784,837 A | 1/1974 | Holmstrom |
| 3,898,463 A | 8/1975 | Noakes |
| 3,904,923 A | 9/1975 | Schwartz |
| 3,914,614 A | 10/1975 | Martone |
| 4,020,346 A | 4/1977 | Dennis |
| 4,047,035 A | 9/1977 | Dennhoven |
| 4,122,783 A | 10/1978 | Pretini |
| 4,139,771 A | 2/1979 | Dennhoven |
| 4,210,811 A | 7/1980 | Dennhoven |
| 4,216,499 A | 8/1980 | Dennhoven et al. |
| 4,254,599 A | 3/1981 | Maistre |
| 4,320,380 A | 3/1982 | Berard |
| 4,366,382 A | 12/1982 | Kotowski |
| 4,399,403 A | 8/1983 | Strandberg |
| 4,430,568 A | 2/1984 | Yoshida |
| 4,471,343 A | 9/1984 | Lemelson |
| 4,497,768 A | 2/1985 | Caldwell |
| 4,563,707 A | 1/1986 | Kishida |
| 4,566,113 A | 1/1986 | Donges |
| 4,599,740 A | 7/1986 | Cable |
| 4,626,688 A | 12/1986 | Barnes |
| 4,634,568 A | 1/1987 | Wimpee |
| 4,641,330 A | 2/1987 | Herwig |
| 4,667,107 A | 5/1987 | Wang |
| 4,709,382 A | 11/1987 | Sones |
| 4,719,153 A | 1/1988 | Akasawa |
| 4,736,401 A | 4/1988 | Donges |
| 4,745,631 A | 5/1988 | Paolini |
| 4,754,469 A | 6/1988 | Harding |
| 4,788,704 A | 11/1988 | Donges |
| 4,789,930 A | 12/1988 | Sones |
| 4,817,123 A | 3/1989 | Sones |
| 4,825,454 A | 4/1989 | Annis |
| 4,853,595 A | 8/1989 | Alfano |
| 4,872,188 A | 10/1989 | Lauro |
| 4,884,289 A | 11/1989 | Glockmann |
| 4,897,550 A | 1/1990 | Bernard |
| 4,956,856 A | 9/1990 | Harding |
| 4,975,917 A | 12/1990 | Villa |
| 4,975,968 A | 12/1990 | Yukl |
| 4,979,202 A | 12/1990 | Siczek |
| 4,991,189 A | 2/1991 | Boomgaarden |
| 5,006,299 A | 4/1991 | Gozani |
| 5,007,072 A | 4/1991 | Jenkins |
| 5,008,911 A | 4/1991 | Harding |
| 5,014,293 A | 5/1991 | Boyd |
| 5,022,062 A | 6/1991 | Annis |
| 5,038,370 A | 8/1991 | Harding |
| 5,046,846 A | 9/1991 | Ray |
| 5,065,418 A | 11/1991 | Bermbach |
| 5,076,993 A | 12/1991 | Sawa |
| 5,078,952 A | 1/1992 | Gozani |
| 5,081,456 A | 1/1992 | Michiguchi |
| 5,091,924 A | 2/1992 | Bermbach |
| 5,098,640 A | 3/1992 | Gozani |
| 5,114,662 A | 5/1992 | Gozani |
| 5,153,439 A | 10/1992 | Gozani |
| 5,162,096 A | 11/1992 | Gozani |
| 5,179,581 A | 1/1993 | Annis |
| 5,181,234 A | 1/1993 | Smith |
| 5,182,764 A | 1/1993 | Peschmann |
| 5,185,778 A | 2/1993 | Magram |
| 5,202,932 A | 4/1993 | Cambier |
| 5,221,843 A | 6/1993 | Alvarez |
| 5,224,144 A | 6/1993 | Annis |
| 5,227,800 A | 7/1993 | Huguenin |
| 5,237,598 A | 8/1993 | Albert |
| 5,247,561 A | 9/1993 | Kotowski |
| 5,253,283 A | 10/1993 | Annis |
| 5,263,075 A | 11/1993 | McGann |
| 5,265,144 A | 11/1993 | Harding |
| 5,313,511 A | 5/1994 | Annis |
| 5,339,080 A | 8/1994 | Steinway |
| 5,345,240 A | 9/1994 | Frazier |
| 5,367,552 A | 11/1994 | Peschmann |
| 5,379,334 A | 1/1995 | Zimmer |
| 5,388,128 A | 2/1995 | Gozani |
| 5,420,905 A | 5/1995 | Bertozzi |
| 5,428,657 A | 6/1995 | Papanicolopoulos |
| 5,493,596 A | 2/1996 | Annis |
| 5,524,133 A | 6/1996 | Neale |
| 5,548,123 A | 8/1996 | Perez-Mendez |
| 5,548,630 A | 8/1996 | Hell |
| 5,552,705 A | 9/1996 | Keller |
| 5,557,283 A | 9/1996 | Sheen |
| 5,600,303 A | 2/1997 | Husseiny |
| 5,600,700 A | 2/1997 | Krug |
| 5,602,894 A | 2/1997 | Bardash |
| 5,606,167 A | 2/1997 | Miller |
| 5,608,214 A | 3/1997 | Baron |
| 5,638,420 A | 6/1997 | Armistead |
| 5,642,393 A | 6/1997 | Krug |
| 5,642,394 A | 6/1997 | Rothschild |
| 5,666,393 A | 9/1997 | Annis |
| 5,687,210 A | 11/1997 | Maitrejean |
| 5,687,717 A | 11/1997 | Halpern |
| 5,689,239 A | 11/1997 | Turner |
| 5,692,028 A | 11/1997 | Geus |
| 5,696,806 A | 12/1997 | Grodzins |
| 5,744,919 A | 4/1998 | Mishin |
| 5,745,543 A | 4/1998 | De Bokx |
| 5,751,837 A | 5/1998 | Watanabe |
| 5,757,472 A | 5/1998 | Wangler |
| 5,763,903 A | 6/1998 | Mandai |
| 5,764,683 A | 6/1998 | Swift |
| 5,768,334 A | 6/1998 | Maitrejean |
| 5,787,145 A | 7/1998 | Geus |
| 5,805,660 A | 9/1998 | Perion |
| 5,838,758 A | 11/1998 | Krug |
| 5,838,759 A | 11/1998 | Armistead |
| 5,854,531 A | 12/1998 | Young |
| 5,903,623 A | 5/1999 | Swift |
| 5,910,973 A | 6/1999 | Grodzins |
| 5,930,326 A | 7/1999 | Rothschild |
| 5,940,468 A | 8/1999 | Huang |
| 5,974,111 A * | 10/1999 | Krug ............... G01N 23/20 378/53 |
| 6,011,266 A | 1/2000 | Bell |
| 6,026,135 A | 2/2000 | McFee |
| 6,031,890 A | 2/2000 | Bermbach |
| 6,054,712 A | 4/2000 | Komardin |
| 6,058,158 A | 5/2000 | Eiler |
| 6,067,344 A | 5/2000 | Grodzins |
| 6,069,936 A | 5/2000 | Bjorkholm |
| 6,081,580 A | 6/2000 | Grodzins |
| 6,094,472 A | 7/2000 | Smith |
| 6,115,128 A | 9/2000 | Vann |
| 6,118,850 A | 9/2000 | Mayo |
| 6,125,165 A | 9/2000 | Warburton |
| 6,128,365 A | 10/2000 | Bechwati |
| 6,151,381 A | 11/2000 | Grodzins |
| 6,184,841 B1 | 2/2001 | Shober |
| 6,188,743 B1 | 2/2001 | Tybinkowski |
| 6,188,747 B1 | 2/2001 | Geus |
| 6,192,101 B1 | 2/2001 | Grodzins |

(56) References Cited

U.S. PATENT DOCUMENTS

| | | |
|---|---|---|
| 6,192,104 B1 | 2/2001 | Adams |
| 6,195,413 B1 | 2/2001 | Geus |
| 6,198,795 B1 | 3/2001 | Naumann |
| 6,216,540 B1 | 4/2001 | Nelson |
| 6,218,943 B1 | 4/2001 | Ellenbogen |
| 6,249,567 B1 | 6/2001 | Rothschild |
| 6,252,929 B1 | 6/2001 | Swift |
| 6,256,369 B1 | 7/2001 | Lai |
| 6,278,115 B1 | 8/2001 | Annis |
| 6,282,260 B1 | 8/2001 | Grodzins |
| 6,288,676 B1 | 9/2001 | Maloney |
| 6,292,533 B1 | 9/2001 | Swift |
| 6,301,326 B2 | 10/2001 | Bjorkholm |
| 6,320,933 B1 | 11/2001 | Grodzins |
| 6,342,696 B1 | 1/2002 | Chadwick |
| 6,347,132 B1 | 2/2002 | Annis |
| 6,356,620 B1 | 3/2002 | Rothschild |
| 6,359,582 B1 | 3/2002 | MacAleese |
| 6,359,597 B2 | 3/2002 | Haj-Yousef |
| 6,373,066 B1 | 4/2002 | Penn |
| 6,417,797 B1 | 7/2002 | Cousins |
| 6,418,194 B1 | 7/2002 | McPherson |
| 6,421,420 B1 | 7/2002 | Grodzins |
| 6,424,695 B1 | 7/2002 | Grodzins |
| 6,434,219 B1 | 8/2002 | Rothschild |
| 6,435,715 B1 | 8/2002 | Betz |
| 6,442,233 B1 | 8/2002 | Grodzins |
| 6,445,765 B1 | 9/2002 | Frank |
| 6,448,564 B1 | 9/2002 | Johnson |
| 6,453,003 B1 | 9/2002 | Springer |
| 6,453,007 B2 | 9/2002 | Adams |
| 6,456,093 B1 | 9/2002 | Merkel |
| 6,456,684 B1 | 9/2002 | Mun |
| 6,459,761 B1 | 10/2002 | Grodzins |
| 6,459,764 B1 | 10/2002 | Chalmers |
| 6,469,624 B1 | 10/2002 | Whan |
| 6,473,487 B1 | 10/2002 | Le |
| RE37,899 E | 11/2002 | Grodzins |
| 6,480,141 B1 | 11/2002 | Toth |
| 6,483,894 B2 | 11/2002 | Hartick |
| 6,501,414 B2 | 12/2002 | Arndt |
| 6,507,025 B1 | 1/2003 | Verbinski |
| 6,532,276 B1 | 3/2003 | Hartick |
| 6,542,574 B2 | 4/2003 | Grodzins |
| 6,542,578 B2 | 4/2003 | Ries |
| 6,542,580 B1 | 4/2003 | Carver |
| 6,546,072 B1 | 4/2003 | Chalmers |
| 6,552,346 B2 | 4/2003 | Verbinski |
| 6,556,653 B2 | 4/2003 | Hussein |
| 6,563,903 B2 | 5/2003 | Kang |
| 6,567,496 B1 | 5/2003 | Sychev |
| 6,580,079 B1 | 6/2003 | Craig |
| 6,580,778 B2 | 6/2003 | Meder |
| 6,584,170 B2 | 6/2003 | Aust |
| 6,597,760 B2 | 7/2003 | Beneke |
| 6,605,473 B1 | 8/2003 | Hajduk |
| 6,606,516 B2 | 8/2003 | Levine |
| 6,621,888 B2 | 9/2003 | Grodzins |
| 6,628,745 B1 | 9/2003 | Annis |
| 6,636,581 B2 | 10/2003 | Sorenson |
| 6,650,276 B2 | 11/2003 | Lawless |
| 6,653,588 B1 | 11/2003 | Gillard-Hickman |
| 6,658,087 B2 | 12/2003 | Chalmers |
| 6,663,280 B2 | 12/2003 | Doenges |
| 6,665,373 B1 | 12/2003 | Kotowski |
| 6,665,433 B2 | 12/2003 | Roder |
| 6,727,506 B2 | 4/2004 | Mallette |
| 6,735,477 B2 | 5/2004 | Levine |
| 6,744,845 B2 | 6/2004 | Harding |
| 6,763,635 B1 | 7/2004 | Lowman |
| 6,765,527 B2 | 7/2004 | Jablonski |
| 6,768,317 B2 | 7/2004 | Moeller |
| 6,785,357 B2 | 8/2004 | Bernardi |
| 6,796,944 B2 | 9/2004 | Hall |
| 6,798,863 B2 | 9/2004 | Sato |
| 6,812,426 B1 | 11/2004 | Kotowski |
| 6,816,571 B2 | 11/2004 | Bijjani |
| 6,831,590 B1 | 12/2004 | Steinway |
| 6,837,422 B1 | 1/2005 | Meder |
| 6,839,134 B2 | 1/2005 | Saito |
| 6,839,403 B1 | 1/2005 | Kotowski |
| 6,843,599 B2 | 1/2005 | Le |
| 6,856,271 B1 | 2/2005 | Hausner |
| 6,876,322 B2 | 4/2005 | Keller |
| 6,891,381 B2 | 5/2005 | Bailey |
| 6,894,636 B2 | 5/2005 | Anderton |
| 6,920,197 B2 | 7/2005 | Kang |
| 6,922,460 B2 | 7/2005 | Skatter |
| 6,924,487 B2 | 8/2005 | Bolozdynya |
| 6,928,141 B2 | 8/2005 | Carver |
| 6,960,019 B2 | 11/2005 | Dammann |
| 6,965,314 B2 | 11/2005 | Bohinc, Jr. |
| 6,973,158 B2 | 12/2005 | Besson |
| 6,987,833 B2 | 1/2006 | Du |
| 7,010,094 B2 | 3/2006 | Grodzins |
| 7,039,159 B2 | 5/2006 | Muenchau |
| 7,045,788 B2 | 5/2006 | Iwatschenko-Borho |
| 7,066,023 B2 | 6/2006 | Herzen |
| 7,092,485 B2 | 8/2006 | Kravis |
| 7,099,434 B2 | 8/2006 | Adams |
| 7,103,137 B2 | 9/2006 | Seppi |
| 7,116,235 B2 | 10/2006 | Alioto |
| 7,130,484 B2 | 10/2006 | August |
| RE39,396 E | 11/2006 | Swift |
| 7,151,447 B1 | 12/2006 | Willms |
| 7,166,844 B1 | 1/2007 | Gormley |
| 7,207,713 B2 | 4/2007 | Lowman |
| 7,218,704 B1 | 5/2007 | Adams |
| 7,238,951 B2 | 7/2007 | Disdier |
| 7,244,947 B2 | 7/2007 | Polichar |
| 7,250,940 B2 | 7/2007 | Jayanetti |
| 7,260,255 B2 | 8/2007 | Polichar |
| 7,277,526 B2 | 10/2007 | Rifkin |
| 7,286,638 B2 | 10/2007 | Ledoux |
| 7,322,745 B2 | 1/2008 | Agrawal |
| 7,335,891 B2 | 2/2008 | Kniss |
| 7,352,843 B2 | 4/2008 | Hu |
| 7,356,115 B2 | 4/2008 | Ford |
| 7,366,282 B2 | 4/2008 | Peschmann |
| 7,368,717 B2 | 5/2008 | Verbinski |
| 7,369,642 B2 | 5/2008 | Eilbert |
| 7,369,643 B2 | 5/2008 | Kotowski |
| 7,372,040 B2 | 5/2008 | Polichar |
| 7,381,962 B2 | 6/2008 | Goldberg |
| 7,400,701 B1 | 7/2008 | Cason |
| 7,406,192 B2 | 7/2008 | Schmiegel |
| 7,417,440 B2 | 8/2008 | Peschmann |
| 7,420,174 B2 | 9/2008 | Kurita |
| 7,420,175 B2 | 9/2008 | Chu |
| 7,440,544 B2 | 10/2008 | Scheinman |
| 7,453,987 B1 | 11/2008 | Richardson |
| 7,461,032 B2 | 12/2008 | Heaton |
| 7,483,511 B2 | 1/2009 | Bendahan |
| 7,492,228 B2 | 2/2009 | Strange |
| 7,492,682 B2 | 2/2009 | Osakabe |
| 7,492,862 B2 | 2/2009 | Bendahan |
| 7,492,934 B2 | 2/2009 | Mundy |
| 7,505,556 B2 | 3/2009 | Chalmers |
| 7,505,557 B2 | 3/2009 | Modica |
| 7,505,562 B2 | 3/2009 | Dinca |
| 7,522,696 B2 | 4/2009 | Imai |
| 7,525,101 B2 | 4/2009 | Grodzins |
| 7,526,064 B2 | 4/2009 | Akery |
| 7,538,325 B2 | 5/2009 | Mishin |
| 7,547,888 B2 | 6/2009 | Cooke |
| 7,551,714 B2 | 6/2009 | Rothschild |
| 7,551,715 B2 | 6/2009 | Rothschild |
| 7,551,718 B2 | 6/2009 | Rothschild |
| 7,555,099 B2 | 6/2009 | Rothschild |
| 7,576,648 B2 | 8/2009 | Harman |
| 7,579,845 B2 | 8/2009 | Peschmann |
| 7,593,506 B2 | 9/2009 | Cason |
| 7,593,510 B2 | 9/2009 | Rothschild |
| 7,606,348 B2 | 10/2009 | Foland |

(56) References Cited

U.S. PATENT DOCUMENTS

| | | |
|---|---|---|
| 7,609,807 B2 | 10/2009 | Leue |
| 7,622,726 B2 | 11/2009 | Zillmer |
| 7,649,976 B2 | 1/2010 | Georgeson |
| 7,652,254 B2 | 1/2010 | Shpantzer |
| 7,653,545 B1 | 1/2010 | Starkie |
| 7,693,261 B2 | 4/2010 | Robinson |
| 7,701,336 B1 | 4/2010 | Willms |
| 7,714,297 B2 | 5/2010 | Morris |
| 7,724,869 B2 | 5/2010 | Wang |
| 7,738,687 B2 | 6/2010 | Tortora |
| 7,741,612 B2 | 6/2010 | Clothier |
| 7,750,294 B2 | 7/2010 | Bright |
| 7,760,103 B2 | 7/2010 | Frank |
| 7,783,003 B2 | 8/2010 | Clayton |
| 7,796,734 B2 | 9/2010 | Mastronardi |
| 7,800,073 B2 | 9/2010 | Clothier |
| 7,809,103 B2 | 10/2010 | Du |
| 7,809,104 B2 | 10/2010 | Foland |
| 7,809,109 B2 | 10/2010 | Mastronardi |
| 7,831,012 B2 | 11/2010 | Foland |
| 7,838,841 B2 | 11/2010 | Morris |
| 7,844,027 B2 | 11/2010 | Harding |
| 7,844,028 B2 | 11/2010 | Korsunsky |
| 7,856,081 B2 | 12/2010 | Peschmann |
| 7,860,213 B2 | 12/2010 | Akery |
| 7,876,879 B2 | 1/2011 | Morton |
| 7,908,121 B2 | 3/2011 | Green |
| 7,915,596 B2 | 3/2011 | Clothier |
| 7,945,105 B1 | 5/2011 | Jaenisch |
| 7,952,079 B2 | 5/2011 | Neustadter |
| 7,957,506 B2 | 6/2011 | Smith |
| 7,965,816 B2 | 6/2011 | Kravis |
| 7,978,804 B2 | 7/2011 | Groves |
| 7,982,191 B2 | 7/2011 | Friedman |
| 7,999,236 B2 | 8/2011 | McDevitt |
| 8,031,903 B2 | 10/2011 | Paresi |
| 8,102,251 B2 | 1/2012 | Webb |
| 8,116,428 B2 | 2/2012 | Gudmundson |
| 8,138,770 B2 | 3/2012 | Peschmann |
| 8,173,970 B2 | 5/2012 | Inbar |
| 8,179,597 B2 | 5/2012 | Namba |
| 8,194,822 B2 | 6/2012 | Rothschild |
| 8,233,586 B1 | 7/2012 | Boas |
| 8,247,767 B2 | 8/2012 | Morris |
| 8,263,938 B2 | 9/2012 | Bjorkholm |
| 8,274,377 B2 | 9/2012 | Smith |
| 8,275,091 B2 | 9/2012 | Morton |
| 8,288,721 B2 | 10/2012 | Morris |
| 8,325,871 B2 | 12/2012 | Grodzins |
| 8,389,941 B2 | 3/2013 | Bendahan |
| 8,389,942 B2 | 3/2013 | Morton |
| 8,428,217 B2 | 4/2013 | Peschmann |
| 8,451,974 B2 | 5/2013 | Morton |
| 8,483,356 B2 | 7/2013 | Bendahan |
| 8,502,699 B2 | 8/2013 | Zerwekh |
| 8,503,605 B2 | 8/2013 | Morton |
| 8,513,601 B2 | 8/2013 | Morris |
| 8,536,527 B2 | 9/2013 | Morris |
| 8,552,370 B2 | 10/2013 | Schultz |
| 8,582,720 B2 | 11/2013 | Morton |
| 8,674,706 B2 | 3/2014 | Peschmann |
| 8,735,833 B2 | 5/2014 | Morto |
| 8,975,593 B1* | 3/2015 | Best .................. G01T 3/008 250/391 |
| 9,042,511 B2 | 5/2015 | Peschmann |
| 9,268,058 B2 | 2/2016 | Peschmann |
| 2002/0008655 A1 | 1/2002 | Haj-Yousef |
| 2002/0130267 A1 | 9/2002 | Odom |
| 2002/0150194 A1 | 10/2002 | Wielopolski |
| 2003/0009202 A1 | 1/2003 | Levine |
| 2003/0118246 A1 | 6/2003 | August |
| 2003/0179126 A1 | 9/2003 | Jablonski |
| 2003/0216644 A1 | 11/2003 | Hall |
| 2004/0017888 A1 | 1/2004 | Seppi |
| 2004/0057042 A1* | 3/2004 | Ovadia .................. G01N 21/88 356/237.1 |
| 2004/0077943 A1 | 4/2004 | Meaney |
| 2004/0086078 A1 | 5/2004 | Adams |
| 2004/0104500 A1 | 6/2004 | Bross |
| 2004/0125914 A1 | 7/2004 | Kang |
| 2004/0140421 A1 | 7/2004 | Dammann |
| 2004/0141584 A1 | 7/2004 | Bernardi |
| 2004/0178339 A1 | 9/2004 | Gentile |
| 2004/0258198 A1 | 12/2004 | Carver |
| 2004/0267114 A1 | 12/2004 | Mundy |
| 2005/0023479 A1 | 2/2005 | Grodzins |
| 2005/0058242 A1 | 3/2005 | Peschmann |
| 2005/0088644 A1 | 4/2005 | Morcom |
| 2005/0104603 A1 | 5/2005 | Peschmann |
| 2005/0105665 A1 | 5/2005 | Grodzins |
| 2005/0117700 A1 | 6/2005 | Peschmann |
| 2005/0120778 A1 | 6/2005 | Von |
| 2005/0135668 A1 | 6/2005 | Polichar |
| 2005/0156734 A1 | 7/2005 | Zerwekh |
| 2005/0157842 A1 | 7/2005 | Agrawal |
| 2005/0161611 A1 | 7/2005 | Disdier |
| 2005/0169421 A1 | 8/2005 | Muenchau |
| 2005/0180542 A1 | 8/2005 | Leue |
| 2005/0220246 A1 | 10/2005 | Masterov |
| 2005/0226383 A1 | 10/2005 | Rifkin |
| 2005/0244116 A1 | 11/2005 | Evans |
| 2005/0275545 A1 | 12/2005 | Alioto |
| 2006/0027751 A1 | 2/2006 | Kurita |
| 2006/0027759 A1 | 2/2006 | Jiang |
| 2006/0145771 A1 | 7/2006 | Strange |
| 2006/0176998 A1 | 8/2006 | Korsunsky |
| 2006/0284094 A1 | 12/2006 | Inbar |
| 2007/0085010 A1 | 4/2007 | Letant |
| 2007/0110215 A1 | 5/2007 | Hu |
| 2007/0140423 A1 | 6/2007 | Foland |
| 2007/0147585 A1 | 6/2007 | Eilbert |
| 2007/0160176 A1 | 7/2007 | Wada |
| 2007/0172129 A1 | 7/2007 | Tortora |
| 2007/0187608 A1 | 8/2007 | Beer |
| 2007/0189454 A1 | 8/2007 | Georgeson |
| 2007/0210255 A1 | 9/2007 | Bjorkholm |
| 2007/0228284 A1 | 10/2007 | Polichar |
| 2007/0241283 A1 | 10/2007 | Chu |
| 2007/0269005 A1 | 11/2007 | Chalmers |
| 2007/0272874 A1 | 11/2007 | Grodzins |
| 2007/0280416 A1 | 12/2007 | Bendahan |
| 2007/0280502 A1 | 12/2007 | Paresi |
| 2007/0286337 A1 | 12/2007 | Wang |
| 2008/0036597 A1 | 2/2008 | Harman |
| 2008/0037707 A1 | 2/2008 | Rothschild |
| 2008/0044801 A1 | 2/2008 | Modica |
| 2008/0048872 A1 | 2/2008 | Frank |
| 2008/0084963 A1 | 4/2008 | Clayton |
| 2008/0128624 A1 | 6/2008 | Cooke |
| 2008/0170655 A1 | 7/2008 | Bendahan |
| 2008/0175351 A1 | 7/2008 | Norman |
| 2008/0191140 A1 | 8/2008 | McDevitt |
| 2008/0283761 A1 | 11/2008 | Robinson |
| 2008/0296519 A1 | 12/2008 | Larsen |
| 2008/0298546 A1 | 12/2008 | Bueno |
| 2008/0304622 A1 | 12/2008 | Morton |
| 2008/0315091 A1* | 12/2008 | Morris .................. G01T 1/18 250/307 |
| 2008/0316017 A1 | 12/2008 | Webb |
| 2009/0001277 A1 | 1/2009 | Payne |
| 2009/0045348 A1 | 2/2009 | Stuenkel |
| 2009/0086314 A1 | 4/2009 | Namba |
| 2009/0101824 A1 | 4/2009 | Beken |
| 2009/0127459 A1 | 5/2009 | Neustadter |
| 2009/0134334 A1 | 5/2009 | Nelson |
| 2009/0140158 A1 | 6/2009 | Clothier |
| 2009/0175412 A1 | 7/2009 | Grodzins |
| 2009/0200480 A1 | 8/2009 | Clothier |
| 2009/0238336 A1 | 9/2009 | Akery |
| 2009/0257555 A1 | 10/2009 | Chalmers |
| 2009/0295576 A1 | 12/2009 | Shpantzer |
| 2009/0321653 A1* | 12/2009 | Perticone ............. G01V 5/0091 250/393 |

(56) References Cited

U.S. PATENT DOCUMENTS

| | | | |
|---|---|---|---|
| 2010/0002834 A1 | 1/2010 | Gudmundson | |
| 2010/0008666 A1 | 1/2010 | Kovsh | |
| 2010/0025573 A1 | 2/2010 | Hahto | |
| 2010/0034353 A1 | 2/2010 | Kravis | |
| 2010/0065745 A1 | 3/2010 | Goldberg | |
| 2010/0289409 A1 | 11/2010 | Rosenthal | |
| 2010/0295689 A1 | 11/2010 | Armistead | |
| 2010/0301226 A1 | 12/2010 | Lacy | |
| 2011/0038453 A1 | 2/2011 | Morton | |
| 2011/0051996 A1 | 3/2011 | Gudmundson | |
| 2011/0064192 A1 | 3/2011 | Morton | |
| 2011/0075808 A1 | 3/2011 | Rothschild | |
| 2011/0089332 A1 | 4/2011 | Ivan | |
| 2011/0096906 A1 | 4/2011 | Langeveld | |
| 2011/0135060 A1 | 6/2011 | Morton | |
| 2011/0204243 A1 | 8/2011 | Bendahan | |
| 2011/0235777 A1 | 9/2011 | Gozani | |
| 2011/0266451 A1 | 11/2011 | Achtzehn | |
| 2011/0266643 A1 | 11/2011 | Engelmann | |
| 2011/0291014 A1 | 12/2011 | Kusner | |
| 2011/0305318 A1 | 12/2011 | Robinson | |
| 2012/0223242 A1 | 9/2012 | Brown | |
| 2012/0236990 A1 | 9/2012 | Rothschild | |
| 2012/0261572 A1 | 10/2012 | Schmidt | |
| 2012/0312985 A1 | 12/2012 | Morris | |
| 2013/0039462 A1* | 2/2013 | Morton | G01V 5/0041 378/57 |
| 2013/0039472 A1 | 2/2013 | Morton | |
| 2013/0081451 A1* | 4/2013 | Kamada | B60P 1/045 73/65.01 |
| 2013/0294574 A1 | 11/2013 | Peschmann | |
| 2013/0343520 A1 | 12/2013 | Grodzins | |
| 2014/0319365 A1 | 10/2014 | Sossong | |
| 2015/0133787 A1 | 5/2015 | Wegner | |
| 2015/0212014 A1 | 7/2015 | Sossong | |
| 2015/0241593 A1 | 8/2015 | Blanpied | |
| 2015/0246244 A1 | 9/2015 | Sossong | |
| 2015/0279489 A1 | 10/2015 | Milner | |
| 2015/0287237 A1 | 10/2015 | Bai | |
| 2015/0325013 A1 | 11/2015 | Patnaik | |
| 2016/0025888 A1 | 1/2016 | Peschmann | |
| 2016/0041297 A1 | 2/2016 | Blanpied | |

FOREIGN PATENT DOCUMENTS

| | | | |
|---|---|---|---|
| CA | 2636306 A1 | 9/2009 | |
| CN | 101443679 A | 5/2009 | |
| CN | 101460003 | 6/2009 | |
| CN | 101504463 | 8/2009 | |
| EP | 0077018 A1 | 4/1983 | |
| EP | 0146255 A2 | 6/1985 | |
| EP | 0176314 | 4/1986 | |
| EP | 0287707 | 10/1988 | |
| EP | 0391237 A1 | 10/1990 | |
| EP | 0919186 A2 | 6/1999 | |
| EP | 1348982 A2 | 10/2003 | |
| EP | 1413898 A1 | 4/2004 | |
| EP | 1526392 | 4/2005 | |
| EP | 1852060 | 11/2007 | |
| EP | 2561346 | 2/2013 | |
| EP | 2663885 | 12/2014 | |
| GB | 516517 A | 1/1940 | |
| GB | 2255634 A | 11/1992 | |
| GB | 2299251 | 9/1996 | |
| GB | 2424065 A | 9/2006 | |
| GB | 2438317 A | 11/2007 | |
| GB | 10017382 | 2/2010 | |
| GB | 2463550 | 3/2010 | |
| JP | 01100493 A | 4/1989 | |
| JP | 2009047559 A | 3/2009 | |
| WO | 9855851 A1 | 12/1998 | |
| WO | 2004010127 A1 | 1/2004 | |
| WO | 2005098400 A2 | 10/2005 | |
| WO | 2005121756 A2 | 12/2005 | |
| WO | 2006036076 A1 | 4/2006 | |
| WO | 2006045019 | 4/2006 | |
| WO | 2006078691 A2 | 7/2006 | |
| WO | 2006095188 | 9/2006 | |
| WO | 2007035359 A2 | 3/2007 | |
| WO | 2007051092 | 5/2007 | |
| WO | 2007068933 A1 | 6/2007 | |
| WO | 2008017983 A2 | 2/2008 | |
| WO | 2009106803 | 9/2009 | |
| WO | 2009137985 | 11/2009 | |
| WO | 2009141613 | 11/2009 | |
| WO | 2009141615 | 11/2009 | |
| WO | 2009150416 A2 | 12/2009 | |
| WO | WO 2011008718 A1 * | 1/2011 | G01V 5/0016 |
| WO | 2011069024 A1 | 6/2011 | |
| WO | 2011087861 | 7/2011 | |
| WO | 2011095810 | 8/2011 | |
| WO | 2011095942 A2 | 8/2011 | |
| WO | 2011106463 A1 | 9/2011 | |
| WO | 2011133384 | 10/2011 | |
| WO | 2011142768 A2 | 11/2011 | |
| WO | 2012109273 | 8/2012 | |
| WO | 2012174265 | 12/2012 | |
| WO | 2013116241 A1 | 8/2013 | |
| WO | 2013181646 A2 | 12/2013 | |
| WO | 2015004471 A1 | 1/2015 | |
| WO | 2015038554 | 3/2015 | |
| WO | 2015057973 | 4/2015 | |

OTHER PUBLICATIONS

International Search Report for PCT/GB2009/001250, Mar. 2, 2010, Rapiscan Security Products Inc.

Mobile X-Ray Inspection Systems, Internet Citation, Feb. 12, 2007, pp. 1-2, URL:http://web.archive.org/web/20070212000928/http://www.bombdetecti- on.com/cat--details.php?catid=20.

Molchanov P A et al: 'Nanosecond gated optical sensors for ocean optic applications' Sensors Applications Symposium, 2006. Proceedings of the 2006 IEEE Houston, Texas,USA February 7-9, 2006, Piscataway, NJ, USA,IEEE, Feb. 7, 2006 ,pp. 147-150, XP010917671 ISBN: 978-0-7803-9580-0.

International Search Report for PCT/US2010/061908, mailed on Apr. 2, 2012, Rapiscan Systems, Inc.

Misso et al., "New developments in radiation detectors and electron multipliers", 1964, IEEE Transactions on Nuclear Science pp. 72-75.

International Search Report for PCT/GB2006/000859, mailed on May 19, 2006, Corus UK Ltd.

Examination Report for GB1212492.1, dated Mar. 16, 2016.

Full Examination Report for Australian Application No. 2013215286, Jul. 30, 2015.

Office Action for Canadian Patent Application No. 2863633, dated Nov. 3, 2015.

First Office Action for Chinese Patent Application No. 2013800149382, dated Dec. 18, 2015.

International Search Report for PCT/US13/23676, Jun. 28, 2013.

Supplementary Partial European Search Report for EP13744250, completed on Sep. 7, 2015.

King et al, 'Development of B-Based He Replacement Neutron Detectors', AIP Conf. Proc. 1412, 216-223 (2011); doi: 10.1063/1.3665317.

Sheen, David et al. 'Three-Dimensional Millimeter-Wave Imaging for Concealed Weapon Detection', Sep. 2001, IEEE Transactions on Microwave Theory and Techniques, vol. 49, No. 9, pp. 1581-1592.

Office Action dated Mar. 18, 2015 for U.S. Appl. No. 14/165,177.

Notice of Allowance dated Aug. 20, 2015 for U.S. Appl. No. 14/165,177.

Notice of Allowance dated Nov. 6, 2015, for U.S. Appl. No. 14/516,146.

Corrected Notice of Allowance dated Mar. 14, 2016 for U.S. Appl. No. 14/516,146.

International Search Report for PCT/US14/60914, mailed on Feb. 4, 2015, Rapiscan Systems Inc.

(56) References Cited

OTHER PUBLICATIONS

Hasuko et al, "The First Integration Test of the Atlas End-Cap Muon Level 1 Trigger System", IEEE Transactions on Nuclear Science, vol. 50, No. 4, Aug. 2003 (2003), pp. 864-868.
Cortesi et al, "Investigations of a THGEM-based imaging detector", Institute of Physics Publishing and SISSA, Sep. 4, 2007.
Notice of Allowance dated Jan. 13, 2015 for U.S. Appl. No. 13/858,479.
Notice of Allowance dated May 14, 2016 for U.S. Appl. No. 14/516,146.
Blanpied et al, "Material discrimination using scattering and stopping of cosmis ray muons and electrons: Differentiating heavier from lighter metals as well as low-atomic weight materials", Nuclear Instruments and Methods Physics Research A, 784 (2015) 352-358.
Office Action dated May 25, 2016 for U.S. Appl. No. 14/591,983.
United States Nuclear Regulatory Commission, "Neutron Detections", Oct. 13, 2010, http://www.nrc.gov/docs/ML1122/ML11229A713.pdf, accessed May 15, 2016.
Notice of Allowance dated Sep. 15, 2016 for U.S. Appl. No. 14/591,983.
Office Action dated May 16, 2016 for U.S. Appl. No. 14/531,437.
International Search Report PCT/US2012/024184, mailed on Jul. 27, 2012, Rapiscan Systems Inc.
International preliminary report on patentability PCT/US2012/024184, issued on Aug. 13, 2013, Rapiscan Systems Inc.
International Search Report PCT/US2012/042493, mailed on Oct. 1, 2012, Rapiscan Systems Inc.
European Search Report for EP12801343.0, Jun. 10, 2015.
Office Action for Canadian Patent Application No. 2,863,363, dated Nov. 3, 2015.
Notice of Allowance mailed Sep. 26, 2016 for U.S. Appl. No. 14/531,437.
International Search Report for PCT/US10/35048; Rapiscan Security Products, Inc.; Feb. 8, 2012.
Third Office Action for CN2011800208127, Jun. 13, 2015.
Fourth Office Action for for CN2011800208127, Aug. 2015.
Office Action dated Jan. 9, 2015 for U.S. Appl. No. 14/268,128.
Notice of Allowance dated Aug. 6, 2015 for U.S. Appl. No. 14/268,128.
International Search Report PCT/US2011/025969, mailed on Aug. 1, 2011, Rapiscan Systems Inc.
Examination Report for GB1215364.9, dated Dec. 4, 2015.
Examination Report for GB1215364.9, May 4, 2016.
Examination Report for GB1215364.9, Sep. 12, 2016.
Jupiter, CP. And Parez, J. "A Study of the Scintillation Properties of Various Hydrogenous and Non-Hydrogenous Solutes Dissolved in Hexafluorobenzene" IEEE Transactions on Nuclear Science, Feb. 1966, pp. 692-703.
Wait, G.D. "A Hexafluorobenzene Gamma Disimeter for Use in Mixed Neutron and Gamma Fields" Jan. 1968, AD0678658, Abstract.
Wolf, A., Moreh, R., "Utilization of teflon-covered GE(Li) diodes for fast neutron detection," Nuclear Instruments and Methods, 148, 1978, 195-197.
Office Action dated Aug. 7, 2015 for U.S. Appl. No. 13/035,886.
Little, R.C.; Chadwick, M. B.; and Myers, W.L. "Detection of Highly Enriched Uranium Through Active Interrogation" Proceedings of the 11th International Conference on Nuclear Reaction Mechanics in Varenna, Italy, Jun. 2006.
Office Action dated Dec. 2, 2015 for U.S. Appl. No. 13/035,886.
"Linac based photofission inspection system employing novel detection concepts", Nuclear Instruments and Methods (2011), vol. 653, Stevenson et al, pp. 124-128.

"Neutron threshold activation detectors (TAD) for the detection of fissions", Nuclear Instruments and Methods in Physics Research (2011), vol. 652, Gozani et al., pp. 334-337.
Examination Report for GB1215374.8, dated Mar. 29, 2016.
Barnabe-Hei Der et al.: 'Characterization of the Response of Superheated Droplet (Bubble) Detectors.' arxic.org, [Online] Nov. 14, 2003, pp. 1-2 Retrieved from the Internet: &ItURL:http://arxiv.org/PS_cache/hep-ex/pdf/0311/0311034v1.pdf> [retrieved on Nov. 8, 2011].
Rolfe et al, "Long Ion Chamber Systems for the SLC" IEEE Particle Accelerator Conference, Chicago, Illinois [online], Mar. 20-23, 1989 [retrieved on Aug. 16, 2011]. Retrieved from the Internet: <URL: http://www.slac.stanford.edu/cgi-wrap/getdoc/slac-pub-4925.pdf> title, abstract, introduction, p. 1 col. 1, para 1, 2, 5; p. 2, col. 1, para 1.
Requirements Letter for Second office action for Mexican Application No. 2012012175, Feb. 5, 2015.
Third Office Action for Mexican Patent Application No. 2012012175, Jul. 22, 2015.
Shafer, Robert E. 'A Tutorial on Beam Loss Monitoring'. Published in Beam Instrumentation Workshop 2002: Tenth Workshop [online] p. 44-58, Smith, G. A., and Russo, T., eds, American Institute of Physics, Brookhaven, May 2002 [retrieved on Aug. 16, 2011]. Retrieved from the Internet: http://ab-div-bdi-bl-blm.web.cern.ch/ab-div-bdi-bl-blm/Beam_loss_detectors/Literature/schaefer_biw02_tutorial.pdf.
International Search Report, PCT/US11/32440, date of mailing Sep. 9, 2011, Rapiscan Systems Inc.
Supplementary European Search Report for EP11760006, Oct. 5, 2016.
Anonymous: "Framebuffer—Wkipedia, the free encyclopedia", Mar. 14, 2010, XP055307861, Retrieved from the Internet: URL: https://en.wikipedia.org/w/index.php?title=Framebuffer &oldid=349748376 [retrieved on Oct. 5, 2016].
Examination Report for GB1220623.1, Rapiscan Systems Inc., May 3, 2016.
International Atomic Energy Agency, Manual for troubleshooting and upgrading of neutron generators. Nov. 1996 [retrieved on Sep. 16, 2013]. Retrieved from the Internet: <URL: http://www-pub.iaea.org/MTCD/publications/PDF/te_913_web.pdf> figures 149-150, pp. 200-203.
Patent Examination Report No. 1 for Australian Patent Application No. 2013267091, dated May 4, 2016.
First Office Action for CN2013800348333, dated Mar. 14, 2016.
Office Action dated Dec. 29, 2014 for U.S. Appl. No. 13/907,811.
International Search Report for PCT/US13/43801, Dec. 6, 2013.
International Search Report for PCT/US10/58809; Rapiscan Systems Inc.; Apr. 19, 2011.
Search and Examination Report for Application No. GB1420349.1, dated Nov. 26, 2014.
Office Action dated Dec. 10, 2012 for U.S. Appl. No. 12/959,356.
Notice of Allowance dated Apr. 22, 2015 for U.S. Appl. No. 13/907,811.
Notice of Allowance dated May 5, 2015 for U.S. Appl. No. 14/047,477.
International Search Report for PCT/GB2014/052110, Dec. 3, 2014.
International Search Report PCT/GB2009/000515, Feb. 23, 2010, Rapiscan Security Products, Inc.
International Search Report for PCT/GB2009/000497, Jan. 22, 2010.
International Search Report PCT/GB2009/001444, Apr. 6, 2010, Rapiscan Security Products.
International Search Report for PCT/GB2009/000556, Feb. 19, 2010, Rapiscan Security Products, Inc.
International Search Report PCT/GB2009/001277, Jul. 20, 2010, Rapiscan Systems, Inc.

* cited by examiner

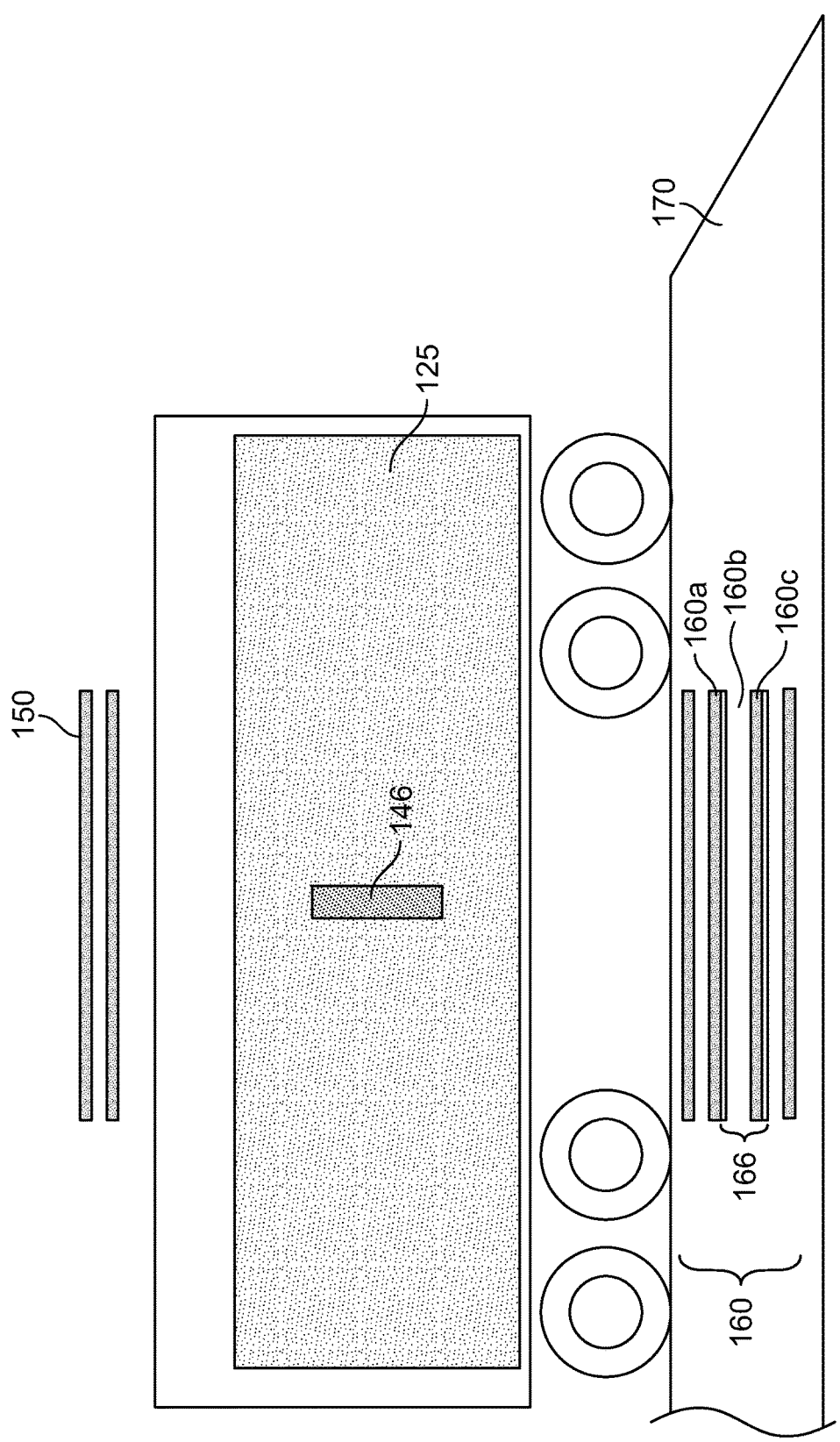

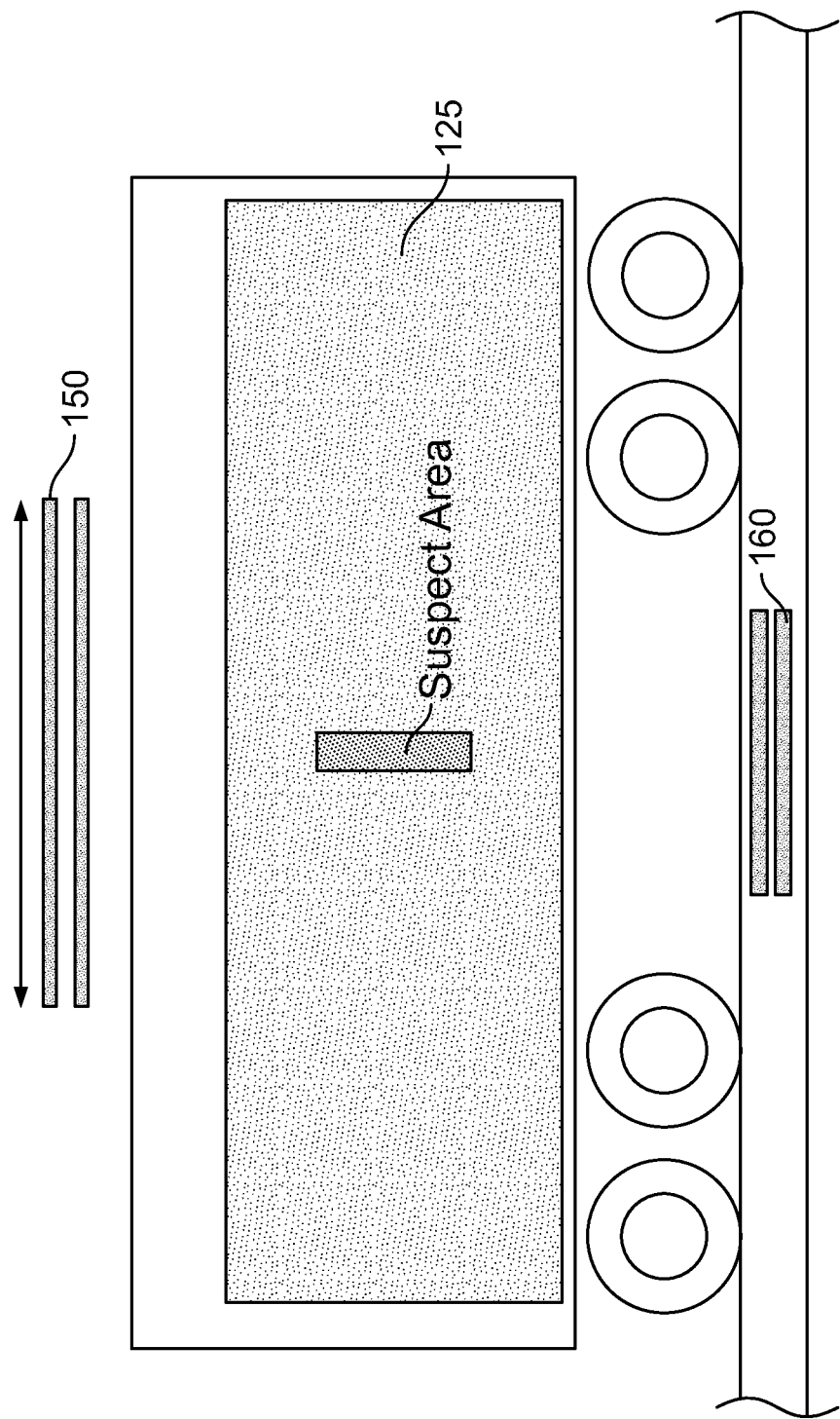

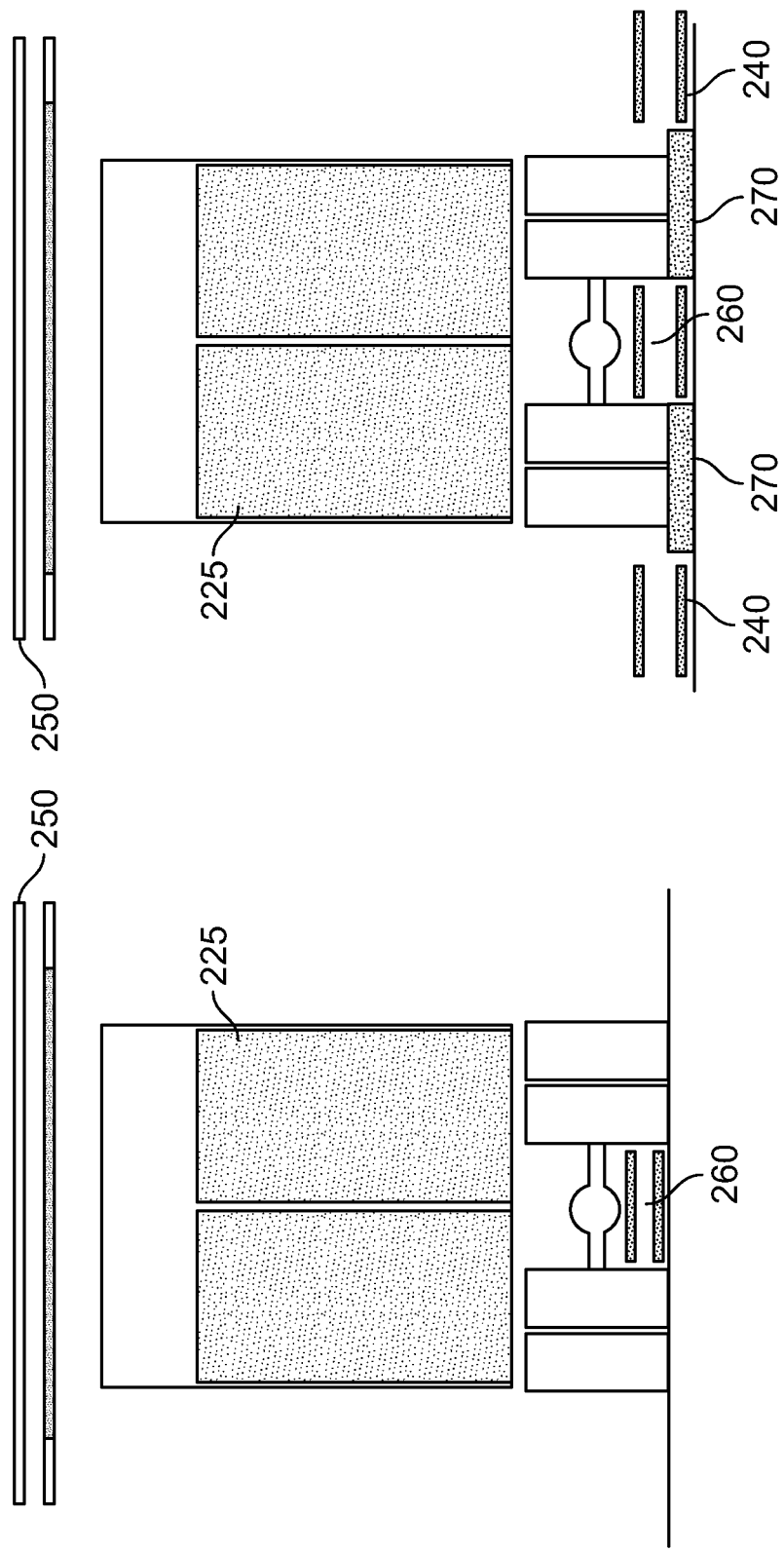

SYSTEMS AND METHODS FOR HIGH-Z THREAT ALARM RESOLUTION

CROSS-REFERENCE

The present application is a continuation application of U.S. patent application Ser. No. 14/516,146, ("146" application) entitled "Systems and Methods for High-Z Threat Alarm Resolution" and filed on Oct. 16, 2014, which relies on U.S. Provisional Patent Application No. 61/891,886, entitled "High-Z Threat Alarm Resolution System and Method", and filed on Oct. 16, 2013, for priority.

The "146" application is also related to U.S. patent application Ser. No. 14/104,625, entitled "Systems and Methods for Automated, Rapid Detection of High-Atomic Number Materials", and filed on Dec. 12, 2013, which is a continuation of U.S. patent application Ser. No. 12/780,910, of the same title and filed on May 16, 2010 and now U.S. Pat. No. 8,633,823, issued on Jan. 21, 2014, which, in turn, relies on U.S. Provisional Patent Application No. 61/178,945, filed on May 16, 2009.

In addition, the "146" application is related to U.S. Pat. Nos. 5,638,420; 6,567,496; 6,785,357; 7,322,745; 7,368,717; and 7,526,064.

All of the above-mentioned patents and patent applications are herein incorporated by reference in their entirety.

FIELD

This specification relates generally to systems for detecting and confirming the presence of high atomic number (high-Z) threats, including shielded and un-shielded special nuclear materials (SNM) and shielded radioactive sources. More particularly, this specification relates to a muon detection system deployed as a second stage of cargo inspection and that uses a plurality of threat sensitivity vectors determined from a first stage of inspection to efficiently and effectively resolve threat alarms.

BACKGROUND

It is a constant challenge to assess the contents of cargo containers using non-intrusive methods. The desire to do so is often fueled by the need to detect contraband and the threats posed, for example, by nuclear weapons. There is a need, therefore, to detect high-Z materials characteristic of shielded radioactive sources and unshielded/shielded special nuclear materials.

Radiation Portal Monitors (RPMs) can detect unshielded or lightly shielded radioactive materials in lightly loaded cargos. However, RPMs cannot detect radioactive sources shielded by high-Z materials, or partially shielded radioactive sources and Uranium-235 in medium-to-heavy cargo. High-energy X-ray inspection systems are widely deployed to detect general contraband and more recently, they have been used to detect shielded and unshielded nuclear materials in cargo.

Current research includes employing Muon Tomography (MT) as a primary inspection system and method for detecting special nuclear materials and shielded radioactive materials. A muon is a charged particle with a mass of 206 times that of the electron with a charge of –1. It has a lifetime of around 6 microseconds, which gives it just enough time to get from the outer edge of the atmosphere, where they are created due to interaction of very energetic protons which arrive at the Earth after travelling billions of miles through deep space, to the surface of the Earth where we can use them for imaging.

Muons are minimum ionizing particles—they lose a bit of their energy by collision with atomic electrons. Thus, the muon travels in a substantially forward direction after each collision, but with a small deviation to the left or the right. After very many collisions, the amplitude of the total deflection from the original direction increases, and this angle of deflection is weakly dependent on the Z (atomic) number of the materials through which the muon is travelling. By measuring the direction of the muon entering a volume and the direction of the muon as it exits the volume, we can draw a line from the point of entrance in the correct direction into the volume and the point of exit in the direction back into the volume and the point of intersection between the two gives the effective center of the scattering material.

However, for detection using Muon Tomography (MT) as a primary inspection system, the throughput is low compared to that for X-ray systems (few minutes vs. tens of seconds). These systems require large detectors that extend the complete object under inspection, which makes the systems expensive and more complex. Also the systems do not provide high-resolution images used to detect general contraband by customs agencies.

Once a high-Z material is detected by a primary system, there is a need to confirm whether the material is fissile. The standard method used for confirmation is based on active interrogation, namely using neutron and/or high-energy sources to induce fission and array of gamma-ray and/or neutrons detectors to detect the radiation emitted from the fission process. However, these systems are complex, expensive, and produce high radiation requiring either a large exclusion zone or a shielded facility.

Therefore, there is a need for a secondary or second stage low-cost system to confirm the presence of shielding and nuclear materials with high confidence in a relatively short time, and with a small exclusion zone compatible with port environments, thereby enabling wide deployment.

SUMMARY

The following embodiments and aspects thereof are described and illustrated in conjunction with systems, tools and methods, which are meant to be exemplary and illustrative, not limiting in scope.

The present specification discloses a second stage screening system to resolve a threat alarm detected in a cargo by a first stage screening system, wherein said first stage screening system generates threat sensitivity vectors, said second stage system comprising: a first muon detector set placed above the cargo to generate first muon information comprising a first coordinate and an angle of incidence of incoming muons; a second muon detector set placed below the cargo to generate second muon information comprising an actual coordinate and an actual angle of exit of the incoming muons; a detector to measure a momentum of said incoming muons; and, a processing unit, wherein said processing unit: receives threat sensitivity vectors determined from the first stage; operates a positioning system that positions a high-Z threat within the cargo relative to said first and second muon detectors; and, employs said first and second muon information and threat sensitivity vectors to confirm a presence of high-Z materials.

The first stage may be a high energy X-ray cargo inspection system.

The first and second muon detectors may be Thin Gap Chamber (TGC) detectors or Thick Gas Electron Multiplier (THGEM) detectors.

Optionally, the threat sensitivity vectors comprise: a number of suspected high-Z threats; an approximate shape and an approximate size of said suspected high-Z threats; dimensional information, density information, and approximate Z distribution of the content of said cargo; and an area or a volume of suspected high-Z threats along a path length of a radiation beam employed for scanning said cargo in said first stage.

Optionally, the positioning system comprises: a range sensor to detect a position of the cargo relative to a center of said first and second muon detectors; and an indicator to assist said cargo in attaining said position. Optionally, the indicator comprises at least one of: a traffic light where green indicates a driver to continue moving, yellow to prepare to stop and red to stop said cargo; and a digital display showing the distance to stop said cargo.

Optionally, the positioning system comprises: a range sensor to detect a position of said cargo relative to a center of said first and second muon detectors; and a detector-positioning system to assist said first and second muon detectors in attaining said position.

The second muon detector may be placed inside a trench in a ground below said cargo.

The cargo may be driven over a ramp wherein said second muon detector is placed within the ramp.

The second muon detector may be sized to be placed in a gap between the wheels of said cargo and two sets of muon detectors may be placed on either side of said cargo. The cargo may be raised over two ramps.

The second muon detector may be positioned vertically on one side of said cargo and the second stage system may further comprise a third muon detector positioned vertically on the other side of said cargo. The second stage system may further comprise at least two layers of fourth muon detectors sized to be placed in a gap between wheels of said cargo. The cargo may be raised over two ramps.

Optionally, said second muon detector has a different size than said first muon detector.

Optionally, said first and second muon detectors comprise at least two layers of detectors that are substantially parallel. The at least two layers of first and second muon detectors may be spaced at a distance ranging from approximately 50 mm to 500 mm.

The first and second muon detectors may have dimensions within a range of approximately 2 m×3 m (length) to 3 m×4 m (width). The first and second muon detectors may have dimensions within a range of approximately 3 m×4 m (length) to 3 m×4 m (width).

Optionally, the processor unit resolves the threat alarm by restricting a muon scan data analysis to an area or volume of said high-Z threat along a path length of a radiation beam employed for scanning said cargo in said first stage.

Optionally, the processor unit uses an approximate Z distribution and density of a content of said cargo to compensate for the presence of cargo content in a vicinity of said high-Z threat.

The first stage may be a radiation portal monitor.

The present specification also discloses a second stage screening system to resolve a threat alarm detected in a cargo by a first stage screening system, the second stage screening system comprising: a first muon detector set placed above the cargo to generate first muon threat information and first muon no-threat information; a second muon detector set placed below the cargo to generate second muon threat information and second muon no-threat information; a detector to measure a momentum of said incoming muons; and a processing unit, wherein said processing unit: receives threat sensitivity vectors determined from the first stage; operates a positioning system that centers a high-Z threat location within the cargo relative to said first and second muon detectors to generate said first and second muon threat information; operates the positioning system that centers a second location within the cargo relative to said first and second muon detectors to generate said first and second no-threat information, wherein the second location has no high-Z threat but has density and Z distribution similar to the high-Z threat location; and, employs said first and second muon threat and no-threat information and threat sensitivity vectors to confirm a presence of high-Z threat.

Optionally, said first muon threat information comprises a first coordinate and an angle of incidence of incoming muons and said second muon threat information comprises an actual coordinate and an actual angle of exit of the incoming muons.

Optionally, said first muon no-threat information comprises a first coordinate and an angle of incidence of incoming muons and said second muon no-threat information comprises an actual coordinate and an actual angle of exit of the incoming muons.

Optionally, the processing unit subtracts the first and second muon no-threat information from the first and second muon threat information to confirm the presence of high-Z threat.

The first stage may be a high energy X-ray cargo inspection system.

The first and second muon detectors may be Thin Gap Chamber (TGC) detectors or Thick Gas Electron Multiplier (THGEM) detectors.

Optionally, the threat sensitivity vectors comprise: a number of suspected high-Z threats; an approximate shape and an approximate size of said suspected high-Z threats; dimensional information, density information, and approximate Z distribution of the content of said cargo; and an area or a volume of suspected high-Z threats along a path length of a radiation beam employed for scanning said cargo in said first stage.

Optionally, the positioning system comprises: a range sensor to detect a position of the cargo relative to a center of said first and second muon detectors; and an indicator to assist said cargo in attaining said position. Optionally, the indicator comprises at least one of: a traffic light where green indicates a driver to continue moving, yellow to prepare to stop and red to stop said cargo; and a digital display showing the distance to stop said cargo.

Optionally, the positioning system comprises: a range sensor to detect a position of said cargo relative to a center of said first and second muon detectors; and a detector-positioning system to assist said first and second muon detectors in attaining said position.

The second muon detector may be placed inside a trench in a ground below said cargo.

The cargo may be driven over a ramp wherein said second muon detector is placed within the ramp.

The second muon detector may be sized to be placed in a gap between the wheels of said cargo and two sets of muon detectors may be placed on either side of said cargo. The cargo may be raised over two ramps.

The second muon detector may be positioned vertically on one side of said cargo and the second stage system may further comprise a third muon detector positioned vertically on the other side of said cargo. The second stage system may further comprise at least two layers of fourth muon detectors sized to be placed in a gap between wheels of said cargo. The cargo may be raised over two ramps.

Optionally, said second muon detector has a different size than said first muon detector.

Optionally, said first and second muon detectors comprise at least two layers of detectors that are substantially parallel.

The at least two layers of first and second muon detectors may be spaced at a distance ranging from approximately 50 mm to 500 mm.

The first and second muon detectors may have dimensions within a range of approximately 2 m×3 m (length) to 3 m×4 m (width). The first and second muon detectors may have dimensions within a range of approximately 3 m×4 m (length) to 3 m×4 m (width).

Optionally, the processor unit resolves the threat alarm by restricting a muon scan data analysis to an area or volume of said high-Z threat along a path length of a radiation beam employed for scanning said cargo in said first stage.

Optionally, the processor unit uses an approximate Z distribution and density of a content of said cargo to compensate for the presence of cargo content in a vicinity of said high-Z threat.

The first stage may be a radiation portal monitor.

The first stage may comprise a single or multi-view x-ray scanner.

The first stage may comprise a Radiation Portal Monitor (RPM) comprising a plurality of radiation detectors that detect radiation emitted by radioactive substances within the cargo being inspected. Optionally, the radiation detectors are oriented vertically in the form of a portal enabling cargo to pass there between. The radiation detectors detect gamma, neutron or a combination of gamma and neutron radiation. Accordingly, the radiation detectors comprise plastic scintillator detectors combined with neutron detector blocks, when desired.

The aforementioned and other embodiments of the present specification shall be described in greater depth in the drawings and detailed description provided below.

BRIEF DESCRIPTION OF THE DRAWINGS

These and other features and advantages of the present specification will be appreciated, as they become better understood by reference to the following detailed description when considered in connection with the accompanying drawings, wherein:

FIG. 1F shows use of scattering layers to measure muon momentum in accordance with an embodiment of the second stage muon detection system;

FIG. 1G shows a third embodiment of the second stage muon detection system;

FIG. 2A shows a fourth embodiment of the second stage muon detection system;

FIG. 2B shows a fifth embodiment of the second stage muon detection system;

DETAILED DESCRIPTION

For purposes of this specification, cargo refers to crates, trucks, vehicles, land or sea containers, pallets and baggage. In one embodiment, the present specification is directed towards a contraband inspection system and method that efficiently detects and resolves high-Z material alarms, such as, but not limited to, special nuclear material(s) (SNM) (i.e. uranium, plutonium) in an assembled nuclear device; at least one separate quantity of SNM(s) intended for the eventual assembly into a nuclear device; and, one of a number of high-Z materials (e.g. tungsten, lead) typically used to shield radioactive materials to prevent the emitted radiation from being detected by the arrays of passive detectors that are being placed into operation at a number of global ports of entry. Examples of radiation-emitting threats include SNM and radioactive isotopes that could be used in a radiological dispersal device (i.e., "dirty bomb").

The present specification is directed towards multiple embodiments. The following disclosure is provided in order to enable a person having ordinary skill in the art to practice the invention. Language used in this specification should not be interpreted as a general disavowal of any one specific embodiment or used to limit the claims beyond the meaning of the terms used therein. The general principles defined herein may be applied to other embodiments and applications without departing from the spirit and scope of the invention. Also, the terminology and phraseology used is for the purpose of describing exemplary embodiments and should not be considered limiting. Thus, the present specification is to be accorded the widest scope encompassing numerous alternatives, modifications and equivalents consistent with the principles and features disclosed. For purpose of clarity, details relating to technical material that is known in the technical fields related to the invention have not been described in detail so as not to unnecessarily obscure the present specification.

Figure 1A:
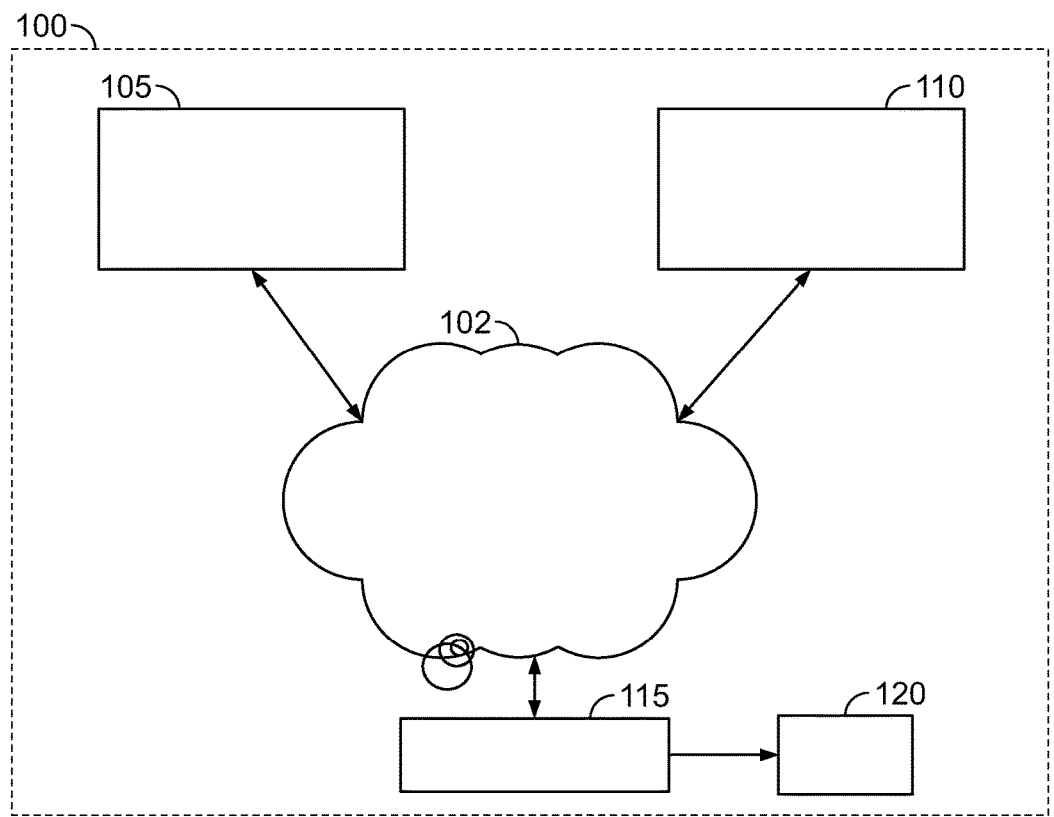
FIG. 1A is a block diagram illustration of a cargo threat detection and alarm resolution system of the present specification.

FIG. 1A is a block diagram illustration of a cargo threat detection and alarm resolution system 100 in accordance with an embodiment of the present specification. The system 100 comprises a muon tomography (MT)-based threat alarm resolution system 110 integrated, associated, linked or coupled with a threat detection system 105. In some embodiments, the threat detection system 105 is operated in a first stage. In some embodiments, the muon tomography system 110 is operated in a second stage. Processor unit 115 uses the data collected from the second stage 110 and the threat detection data from the first stage 105 to confirm or clear a potential threat alarm and to coordinate alignment of the identified threat areas with reference to the second stage muon tomography system 110. Monitor 120 displays a plurality of processed information from the first stage 105 and/or second stage 110.

The first and second stages 105, 110 along with the processor 115 and the monitor 120 are linked through a data communication wired and/or wireless network 102. While in one embodiment, the first and second stages 105, 110 are co-located in another embodiment these are remotely located from each other. When the two stages 105, 110 are placed remotely or at a distance from one another the potential threat alarm scan data from the first stage 105 is communicated to the remotely located second stage 110. Also, in some embodiments, a cargo vehicle license plate or cargo ID is read using an Optical Character Recognition (OCR) or a similar identification system to allow for matching the cargo scan between the two stages 105, 110.

Also, while FIG. 1A shows a single processing unit 115 linked to both stages 105, 110 in alternate embodiments the two stages 105, 110 may have their respective processing units that in turn are linked to each other through a wired and/or wireless network for data communication.

In addition, one of ordinary skill in the art would appreciate that the processing unit 115 comprises any computing platform including, but not limited to: a laptop or tablet computer; personal computer; personal data assistant; cell phone; server; embedded processor; main-frame, DSP chip or specialized imaging device. The threat alarm resolution methods of the present specification are calibrated based on muon scan measurements of a plurality of high-Z materials placed in a plurality of locations within a variety of cargo content and for a plurality of muon momentums. Additionally, the threat alarm resolution methods described herein may be implemented in programmatic code that can be compiled (either pre-compiled or compiled "just-in-time") into a single application executing on a single computer, or distributed among several different computers operating locally or remotely to each other. It should further be appreciated that all of the method steps disclosed herein, including any and all processing or analytical functions, are implemented in such programmatic code stored in a memory and executed on by at least one processor in the computing platform.

Figure 1B:
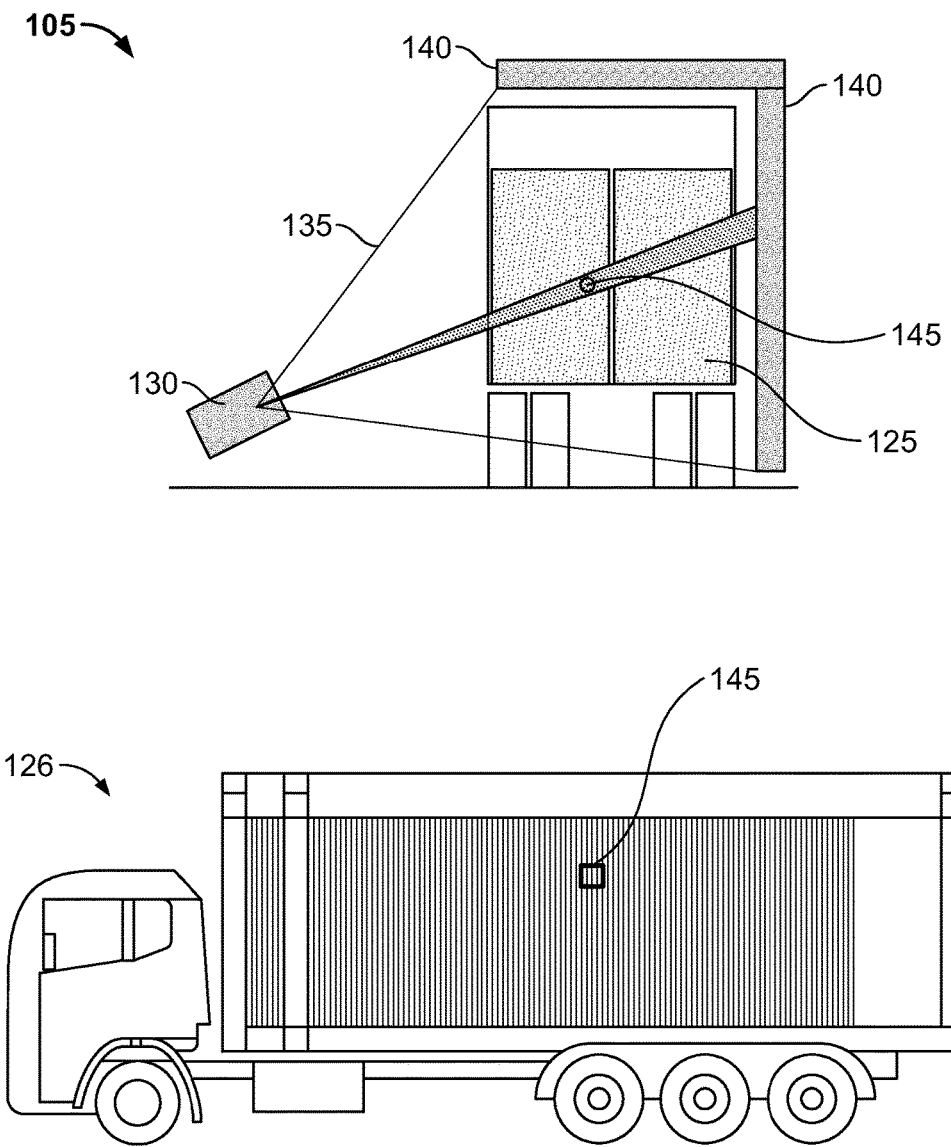
FIG. 1B shows an embodiment of a first stage high energy X-ray cargo inspection system.

In an embodiment, the first stage 105 comprises a high energy X-ray cargo inspection system that scans cargo containers/vehicles at high throughput and determines/detects a presence of areas suspected to contain high-Z materials, including threats such as shielded and un-shielded special nuclear materials (SNM) and radioactive materials. The first stage 105 may employ single, dual or multi-energy, multi-view radiographic imaging systems including those where X-rays or gamma rays, neutrons and both neutrons and X-rays or gamma rays are employed. An advantage of the multi-view radiographic imaging systems is that such systems enable better localization of high-Z threats thereby improving detection at the second stage FIG. 1B shows, in accordance with the first stage 105, a cargo 125 being scanned by a high energy X-ray source 130 such that a fan beam of radiation 135 transmitted through the cargo 125 is captured by detectors 140. In one embodiment, the detectors 140 are oriented such that they form an L-shape. In one embodiment, the source 130 and detectors 140 are stationary while the cargo 125 is made to move there between. In an alternate embodiment, a scan vehicle with an L-shaped boom carries the source 130 with the detectors 140 mounted on the boom. In this case, the scan vehicle is moved with reference to the cargo 125, which remains stationary, for inspection. The processor 115 (shown in FIG. 1A) implements an image processing and threat detection method that processes radiographic scanned image data 126 obtained from the detectors 140 to determine a presence of one or more high-Z threats 145 within the cargo 125. The image processing and threat detection method is calibrated based on measurements of a plurality of high-Z materials placed in a plurality of locations within a variety of cargo content. An example first stage X-ray cargo inspection system and method is described in US Publication No. 20100295689 which is herein incorporated by reference in its entirety.

The cargo distribution is estimated employing the 2D X-ray image 126 and making assumptions about the depth position of the cargo. For dual-energy X-ray systems, the approximate atomic number can also be inferred. Persons of ordinary skill in the art should appreciate that an exact composition of cargo is not required to compensate for the scattering of the cargo. Therefore, in most cases, these estimates would suffice. For multi-view systems, the cargo estimates are more accurate.

In accordance with an embodiment, the radiographic scan data 126 is processed to extract threat sensitivity vectors such as a) number of 'suspected high-Z' objects/threats, b) a plurality of suspected high-Z' parameters such as position/location along the path length of the beam 135, suspected shape, size and c) a plurality of cargo content parameters such as dimensions, density and approximate density and Z distribution of the cargo content in the vicinity of the 'suspected high-Z' areas/objects.

Referring back to FIG. 1A, the second stage 110 comprises a passive cosmic-ray muon detection system. Penetrating cosmic-ray muons are a natural radiation background. When they travel through a material, muons deviate from their original trajectory, the extent of the effect depending on the material atomic number Z and thickness, and on the muon particle momentum.

Figure 1C:
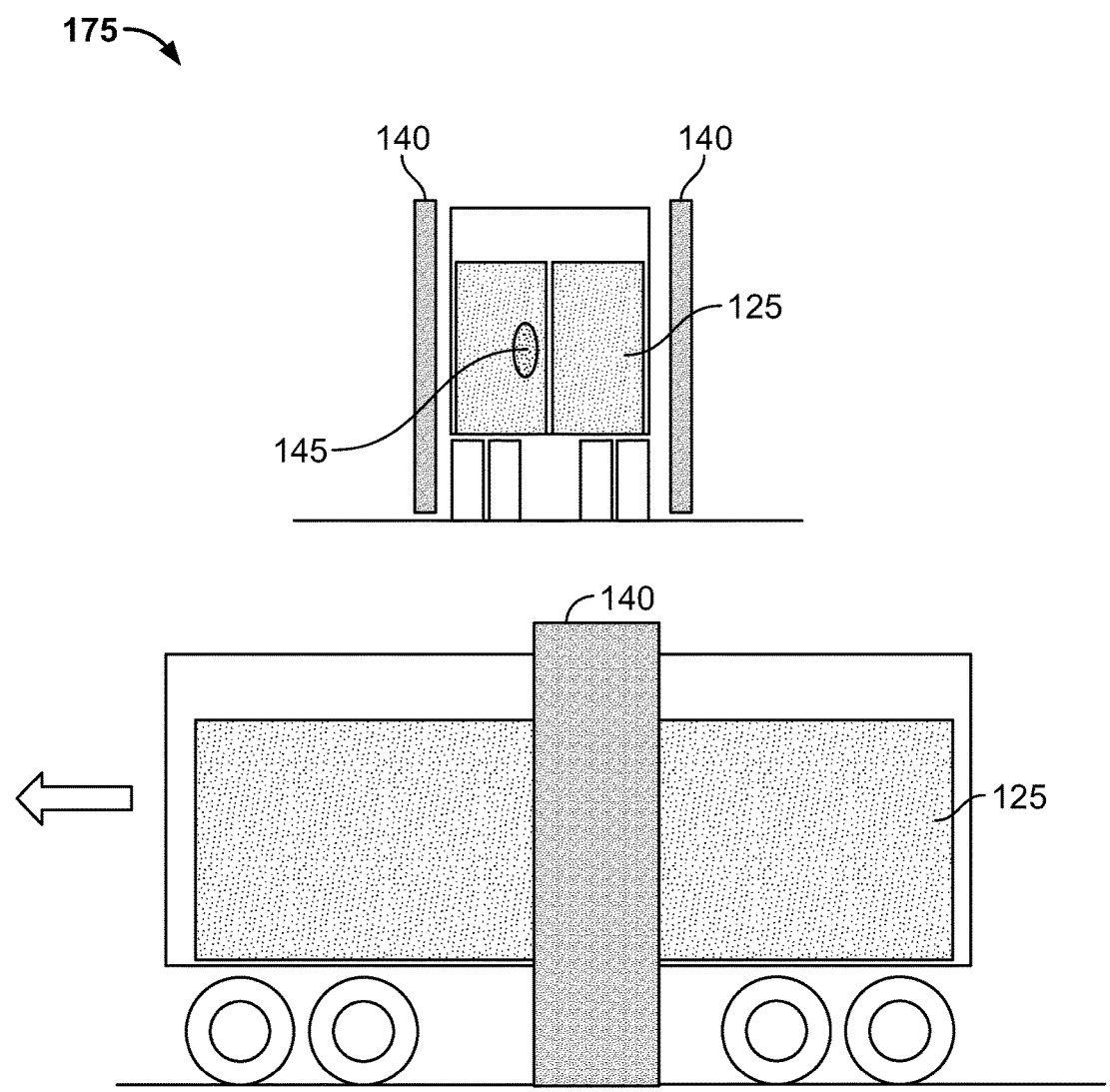
FIG. 1C shows an embodiment of a Radiation Portal Monitor (RPM) of the first stage inspection system.

In one embodiment, the first stage 105 comprises a Radiation Portal Monitor (RPM) comprising a plurality of radiation detectors that detect radiation emitted by radioactive substances within the cargo being inspected. FIG. 1C shows a Radiation Portal Monitor 175 wherein the cargo 125 is being scanned by detectors 140. In one embodiment, the detectors 140 are oriented vertically in the form of a portal enabling the cargo 125 to pass there between. The detectors 140 detect gamma, neutron or a combination of gamma and neutron radiation. Accordingly, the detectors 140 comprise gamma-ray detectors combined with neutron detector blocks, when desired. Example Radiation Portal Monitors include TSA TM850 and TSA VM250 by Rapiscan Systems Inc. The processor 115 (shown in FIG. 1A) implements an image processing and threat detection method that processes radiation scan data obtained from the detectors 140 to determine the presence of special nuclear material 145 within the cargo 125.

Figure 1D:
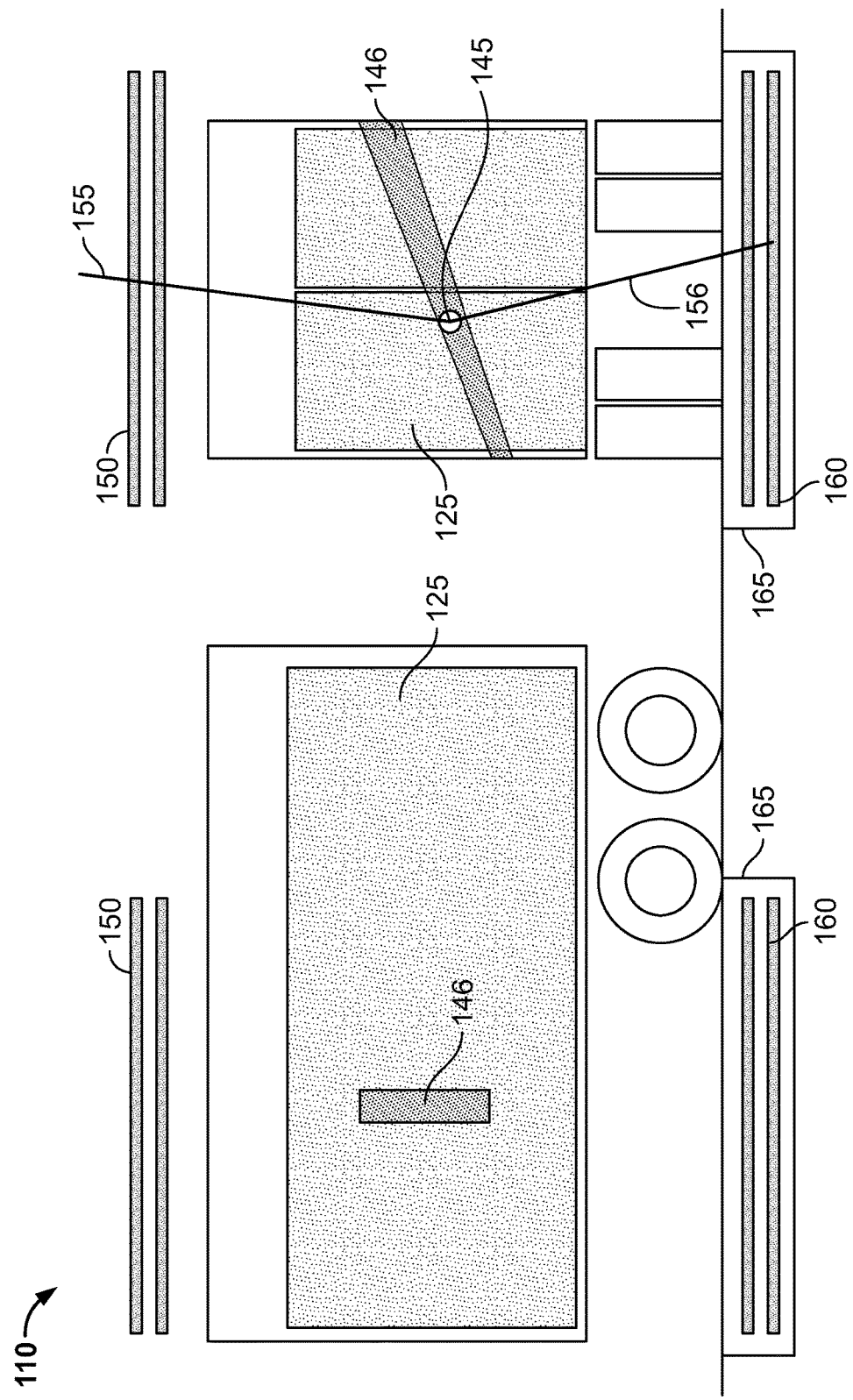
FIG. 1D shows a first embodiment of a second stage muon detection system.

FIG. 1D shows the second stage 110 wherein a single layer muon detector or at least two layers of substantially parallel muon detectors 150 separated by a distance 'd', such as that ranging from approximately 50 mm to 500 mm, and preferably 400 mm, are placed on top of the cargo 125 to detect a direction or angle of incidence of incident muons 155. An additional single layer muon detector or at least two additional layers of substantially parallel muon detectors 160 are placed below the cargo 125 to detect a muon scattering angle or an angle of exit of the scattered muons 156. In one embodiment the dimensions of the detectors ranges from approximately 2 m×3 m (length) to 3 m×4 m (width) so as to enable capturing incident and scattered muons. In other embodiments, where the first stage 105 comprises a Radiation Portal Monitor (as shown in FIG. 1C), the dimensions of the detector 150, 160 ranges from approximately 3 m×4 m (length) to 3 m×4 m (width). In a preferred embodiment, the muon detectors are Thin Gap Chamber (TGC) detectors or Thick Gas Electron Multiplier (THGEM). However, in various alternate embodiments other types of detectors can be used, such as for example—cylindrical proportional counters with pulse shape discriminating readout to maximize spatial resolution. In one embodiment, the bottom detectors 160 are placed inside a trench 165 dug in the ground. This embodiment is useful for fixed second stage sites.

Figure 1E:
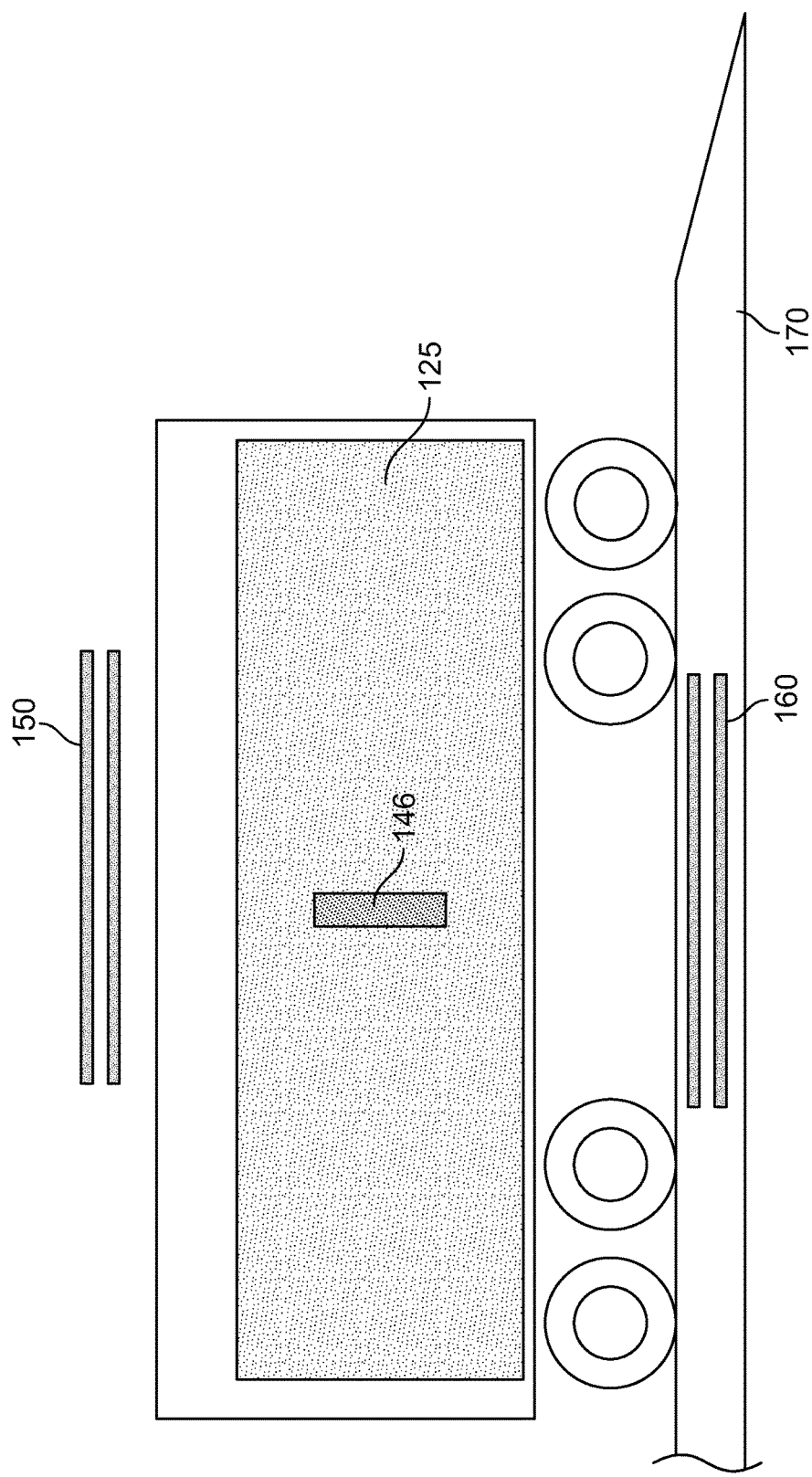
FIG. 1E shows a second embodiment of the second stage muon detection system.

FIG. 1E shows another embodiment, where the cargo 125, comprising a 'suspected high-Z' threat area 146, is driven over a ramp 170 with the detectors 160 placed inside the ramp 170 and with detectors 150 at the top. This embodiment is more suitable when a trench is not desired due to reasons such as low water table, need for a relocatable system, cost, etc. FIG. 1G shows yet another embodiment where the lower detectors 160 are smaller to reduce cost and reduce installation requirements.

The number and orientation of the muon detectors can vary in accordance with a plurality of embodiments. For example, in one embodiment shown in FIG. 2A two muon detectors 250 are placed horizontally at the top while small muon detector layers 260 are placed in the gap between the wheels of the cargo 225. In this case the distance between the detector layers 260 is less thereby reducing the angular resolution. FIG. 2B shows an improved embodiment wherein apart from using the top detectors 250, two low-height ramps 270 (approximately 20 cm to 50 cm in height) are used to raise the cargo vehicle 225 to allow the required spacing between the layers of the bottom detectors 260. These ramps are made for example, of aluminum honeycomb, to reduce weight and facilitate relocation. In one embodiment, the top muon detectors 250 are mounted on a horizontal boom of a muon scanning vehicle. In an additional embodiment, as shown in FIG. 2B, two sets of detectors 240 are additionally placed on each side of the cargo vehicle 225 to increase the detection efficiency. The advantage of the embodiments shown in FIGS. 2A and 2B is a reduction of site modifications, with some increase of scan time due to a loss of efficiency.

Figure 2C:
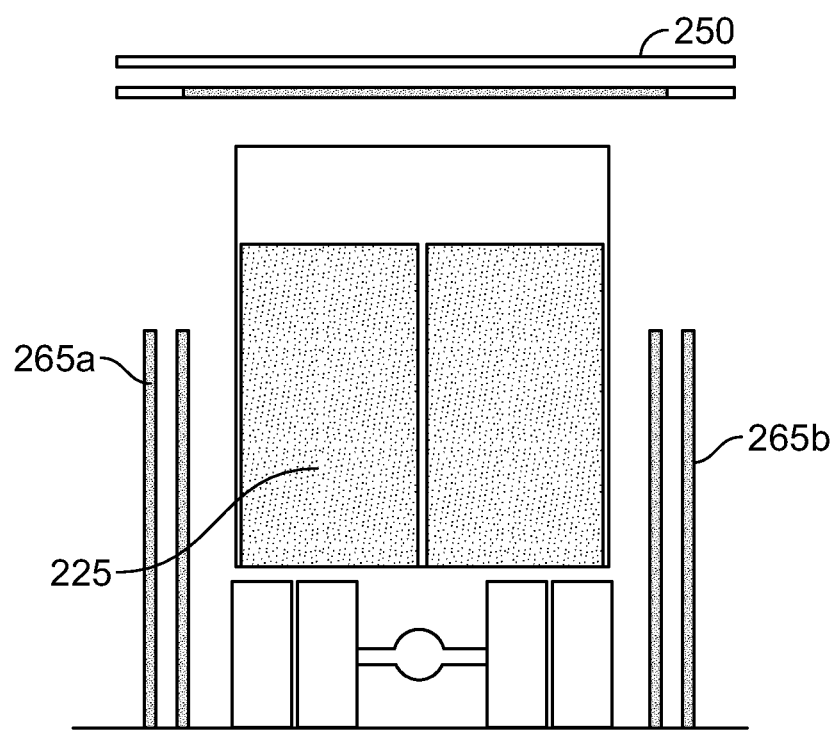
FIG. 2C shows a sixth embodiment of the second stage muon detection system.
Figures 2D, 2E:
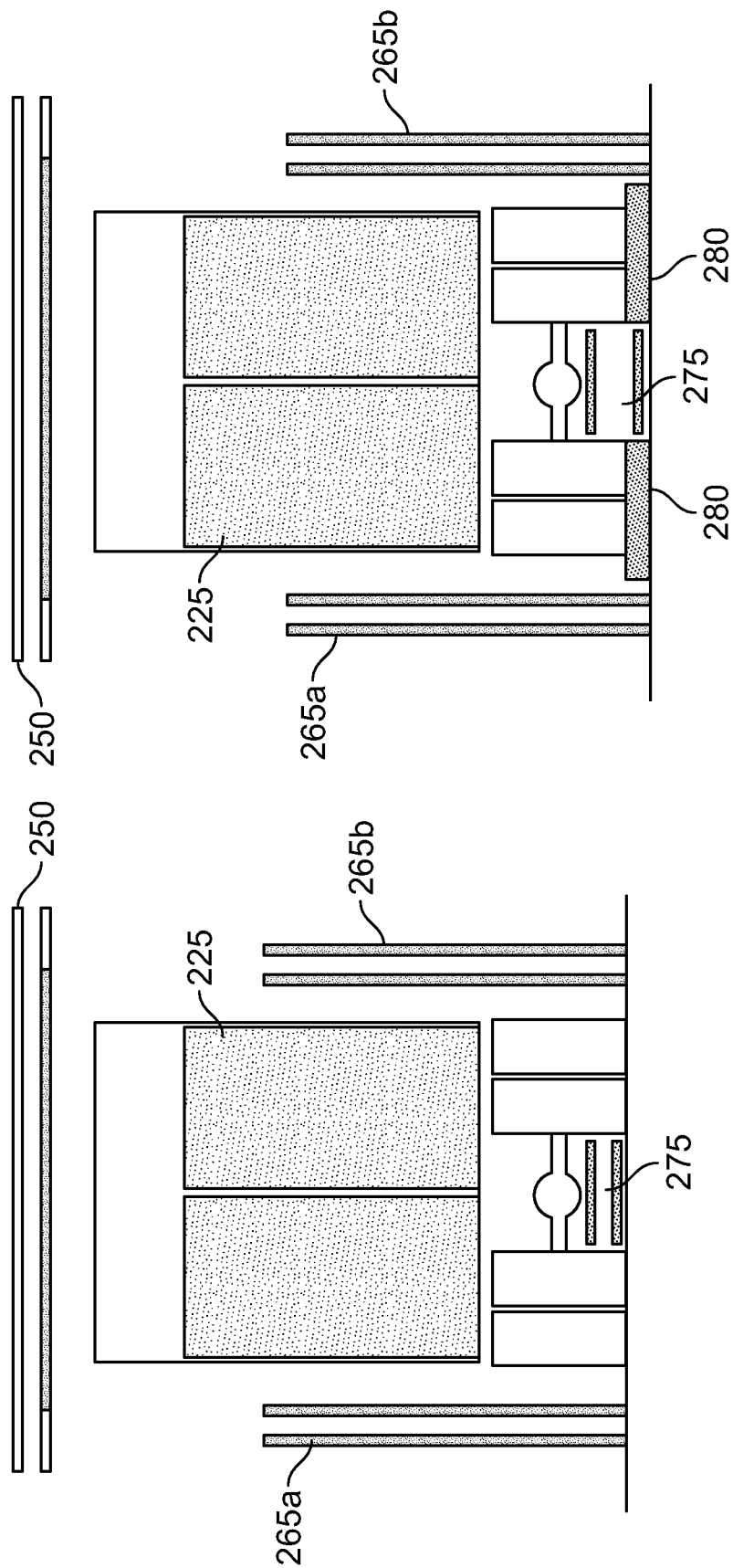
FIG. 2D shows a seventh embodiment of the second stage muon detection system.
FIG. 2E shows an eighth embodiment of the second stage muon detection system.

FIG. 2C shows another embodiment where apart from the top horizontal muon detectors 250 additional muon detectors 265a, 265b are placed vertically at both sides of the cargo 225. In an embodiment, the vertical detector 265a is installed on a side of a muon scanning vehicle while the detectors 250 and 265b are mounted on a horizontal and vertical boom of the scanning vehicle. Alternatively, the detectors 250, 265a, 265b are mounted on a mobile gantry. Improved muon detection efficiency is achieved if apart from the detectors 250, 265a, 265b—small muon detectors 275 are additionally placed in the gap between the wheels of the cargo 225, as shown in FIG. 2D. However, in this case the distance between the detector layers 275 is less thereby reducing the angular resolution. Therefore, in an alternate embodiment, two low-height ramps 280 (approximately 20 cm to 50 cm in height) are used to raise the cargo 225 and allow the required spacing between the layers of the detectors 275 as shown in FIG. 2E. The configuration of detectors 250, 265a, 265b remains same across the embodiments of FIGS. 2C, 2D and 2E.

Referring back to FIG. 1D, the threat sensitivity vectors (from the first stage 105) are utilized advantageously by the second stage 110 to efficiently and effectively resolve threat alarms. For example, the number and position of 'suspected high-Z' threats (of the threat sensitivity vectors) are used to move and position the cargo 125 in such a way that the 'suspected high-Z' threat 145 (within the threat area/volume 146) is centered at the detectors 150 and 160, at which time a stationary and passive muon scan is performed. If there are more than one 'suspected high-Z' threat areas, the above process of threat area alignment with reference to the detectors 150, 160, is repeated. If some or all of the suspected threats are grouped close to each other (such as being less than 0.5 m apart), the detectors 150, 160 are centered at the approximate center of the suspected threats. In one embodiment, the processor 115, shown in FIG. 1A, uses the threat sensitivity vectors to coordinate the operation of a cargo positioning system to enable proper alignment of the 'suspected high-Z' threat areas 146 within the cargo 125 with reference to the detectors 150, 160.

Figure 1H:
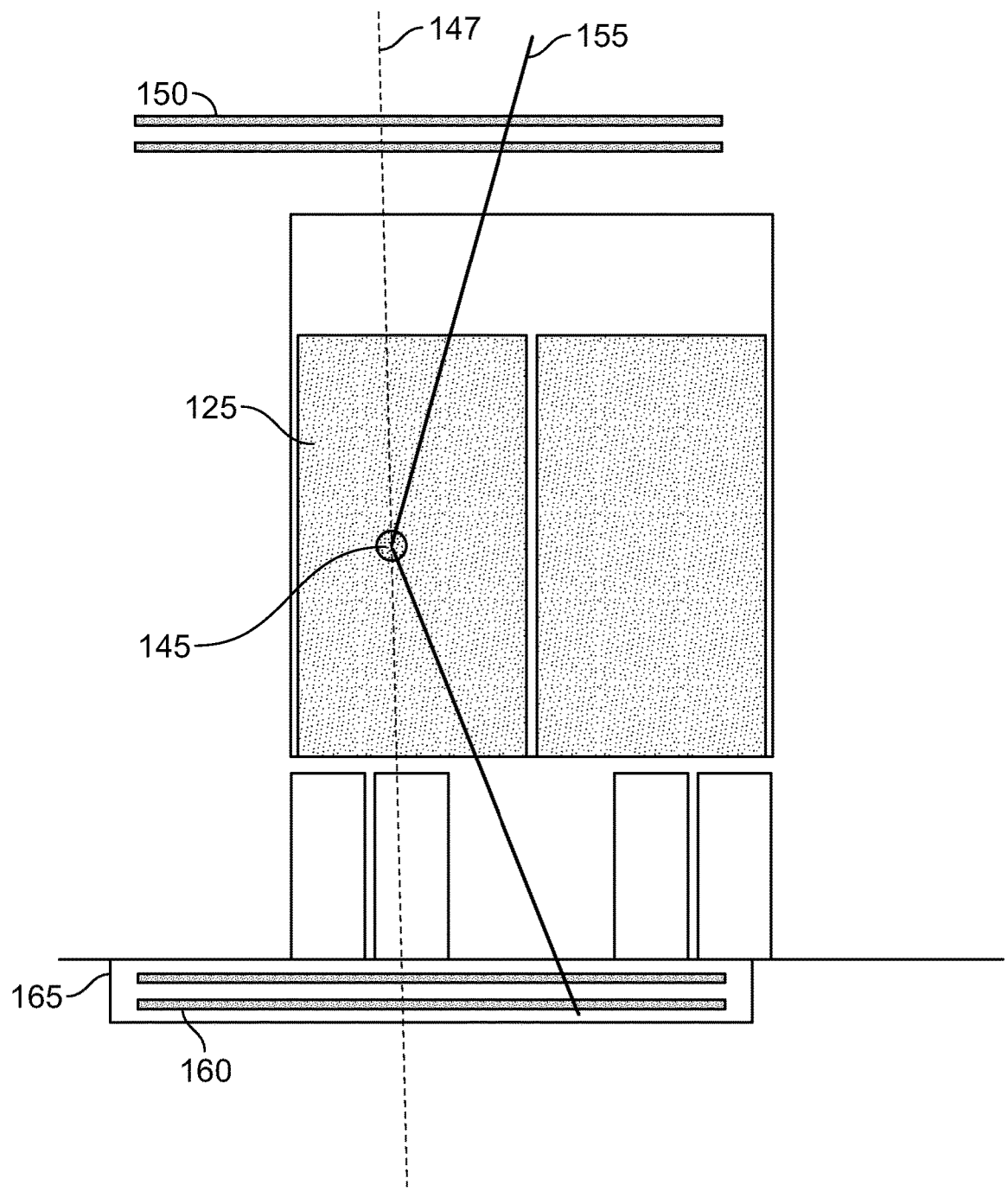
FIG. 1H shows positioning of a cargo for the second stage inspection in accordance with an embodiment.

The cargo positioning system, in one embodiment, comprises a range sensor that detects the position of the cargo 125 relative to the center of the muon detectors 150, 160. Using the position of the 'suspected high-Z' threat 145 (within the threat area/volume 146) obtained from the primary system/first stage 105, an indicator notifies the cargo vehicle driver to stop the cargo where the 'suspected high-Z' alarming threat area(s) is at the approximate center of the muon detectors. In one embodiment, the indicator comprises a traffic light where green indicates to continue moving, yellow to prepare to stop and red to stop. The indicator may also include a digital display that shows the cargo driver the distance to stop. FIG. 1H shows, according to an example, the positioning of the cargo 125 when the first stage 105 provides three dimensional (3D) localization information of the 'suspected high-Z' threat 145. In addition to locating the plane 147 of the threat 145 at the center of the muon detectors 150, 160 (detector 160 being located in a trench 165 in accordance with the embodiment of FIG. 1D) in the direction of motion, the cargo 125 is also positioned in such a way that the threat 145 is centered laterally with reference to the muon detectors 150, 160.

Unlike active interrogation systems, the muon-based detection system being passive enables the cargo driver to stay on the truck, reducing the overhead time to have the driver get off and back on, thereby obviating a need for mechanical systems to move the cargo/container.

In another embodiment, the cargo is stationary and the detectors are moved to be centered at the location of the suspect threat/object. In this embodiment the detectors are housed in a truck ramp to enable appropriate positioning relative to the suspected threat location.

The first muon detectors 150 measure the muon incidence angle and muon incidence coordinate while the second muon detectors 160 measure the actual muon exit angle and muon exit coordinate. In addition to the Z of the materials, the muon deflection/scatter angles also depend on the momentum of the incoming muons, with low-energy muons (e.g. <1 GeV) generating larger deflection/scatter angles than the high-energy muons. Therefore, a measurement of the muon momentum reduces the Z uncertainty. In one embodiment, the low energy muon momentum is also determined by measuring the muon velocity derived from the distance and time of flight between the upper and lower detectors 150, 160.

Another possibility to measure the momentum of the muon is to add scattering layers below the lower detectors 160. As illustrated in FIG. 1F, each scattering layer is built from a layer of lead 166 attached to the muon detector layer above 160a, an empty space 160b (e.g. 25 cm) and another detector layer 160c. The number of scattering layers and the amount of lead define the range and accuracy of the momentum measurements possible with such a detector [as described in L. Shultz, Ph.D. thesis, Portland State University, 2003]. It should be appreciated that the use of scattering layers can be implemented as part of the trench (of FIG. 1D) or the ramp (as shown in FIG. 1F). The empty space 160b between the scattering layer and the detector 160c positioned below it can be increased to allow the use of detectors with lower spatial resolution.

The processor 115, shown in FIG. 1A, implements a threat alarm resolution method of the present specification that, in one embodiment, uses the coordinate and incidence angle parameters for each muon measured at the top detector layers 150 to calculate the expected muon coordinate and exit angle parameters at the bottom detector layers 160. A distribution of the deflection/scatter angles, calculated according to the measurements of the actual incident and exit angles, are compared with the expected parameters. If the deviation between the actual and expected parameters is greater than or equal to a predetermined threshold scattering angle then the second stage 110 confirms the threat alarm determined by the first stage 105 and an audio/visual alarm is generated. However, if the deviation between the actual and expected parameters is below the predetermined threshold then the second stage 110 clears the threat alarm. In one embodiment, the predetermined threshold scattering angle ranges from 1 to 100 milliradian. In other embodiments, if the deflection/scattering angle distribution has an excess of large angle scattering events, then the second stage 110 confirms the threat alarm determined by the first stage 105. Also, alternate embodiments use reconstruction algorithms such as, but not limited to, point of closest approach (POCA) or expectation maximization (EM) to determine the point(s) of muon interaction within the cargo and angle(s) of deflection/scatter. POCA takes the muon's entry and exit coordinates, constructs the entry and exit trajectory, then calculates the line of shortest distance between them and the midpoint of that line is taken to be where scattering took place. This point is given the name POCA point. EM reconstruction uses an iterative method. It takes both scattering angle and linear deviation as input. Then it distributes the scattering location along the POCA track and thereafter determines the maximum likelihood of scattering over voxels.

One of the issues for detecting high-Z materials in cargo is that cargo materials could be dense and occupy a large volume of the cargo container. This results in many small-angle scatters that could be confused with high-Z materials in a lightly loaded cargo. Also, the high-Z materials located at different parts of the cargo result in different muon scatter responses. Therefore, it is highly desirable to have knowledge of the cargo material and distribution, and approximate location of the high-Z materials to compensate for the issues related to cargo material and distribution.

In an embodiment that addresses these issues, the threat alarm resolution method of the present specification additionally utilizes the threat sensitivity vectors of the first stage 105 by a) correlating the 'suspected high-Z' parameters such as position/location, shape and size determined in the first stage 105 with the muon scan data in the second stage 110 and b) building a reference for distribution of muon deflections by employing the cargo content parameters such as dimensions, density and approximate Z distribution of the cargo content in the vicinity of the 'suspected high-Z' areas/objects. Persons of ordinary skill in the art would appreciate that in prior art primary muon measurement systems, the image reconstruction is performed to determine the location of the high-Z materials within the complete volume of the cargo. However, in the threat alarm resolution method of the present specification, the volume to analyze (or the muon scan data to be analyzed) is only the one along the path length of the beam. Also, the X-ray scan image provides useful information about the cargo density and atomic-number (Z) distribution that is used to compensate for the presence of neighboring material. Thus, in this embodiment apart from using the deviation of actual and expected parameters to resolve threat alarms, the threat alarm resolution method of the present specification utilizes the threat sensitivity vectors of the first stage 105 to further improve robustness and effectiveness of the threat alarm resolution thereby reducing false positive alarm rates.

Accordingly, in one embodiment, the muon measurements (that is, the muon incidence angle and the muon incidence coordinate of an incoming muon at the first muon detectors 150 and the actual muon exit angle and the mount exit coordinate of the incoming muon at the second muon detectors 160) are performed at a first and a second location. The first location corresponds to the 'suspected high-Z' threat 145 while the second location is taken (different from the first location) where there is cargo similar to the cargo around the 'suspected high-Z' threat 145 but without the threat. The muon results at the second location, without the threat, are used to compensate for the cargo scattering. In addition, the constraint consisting of the threat location along the path of the radiation is used to improve detection.

Figure 3:
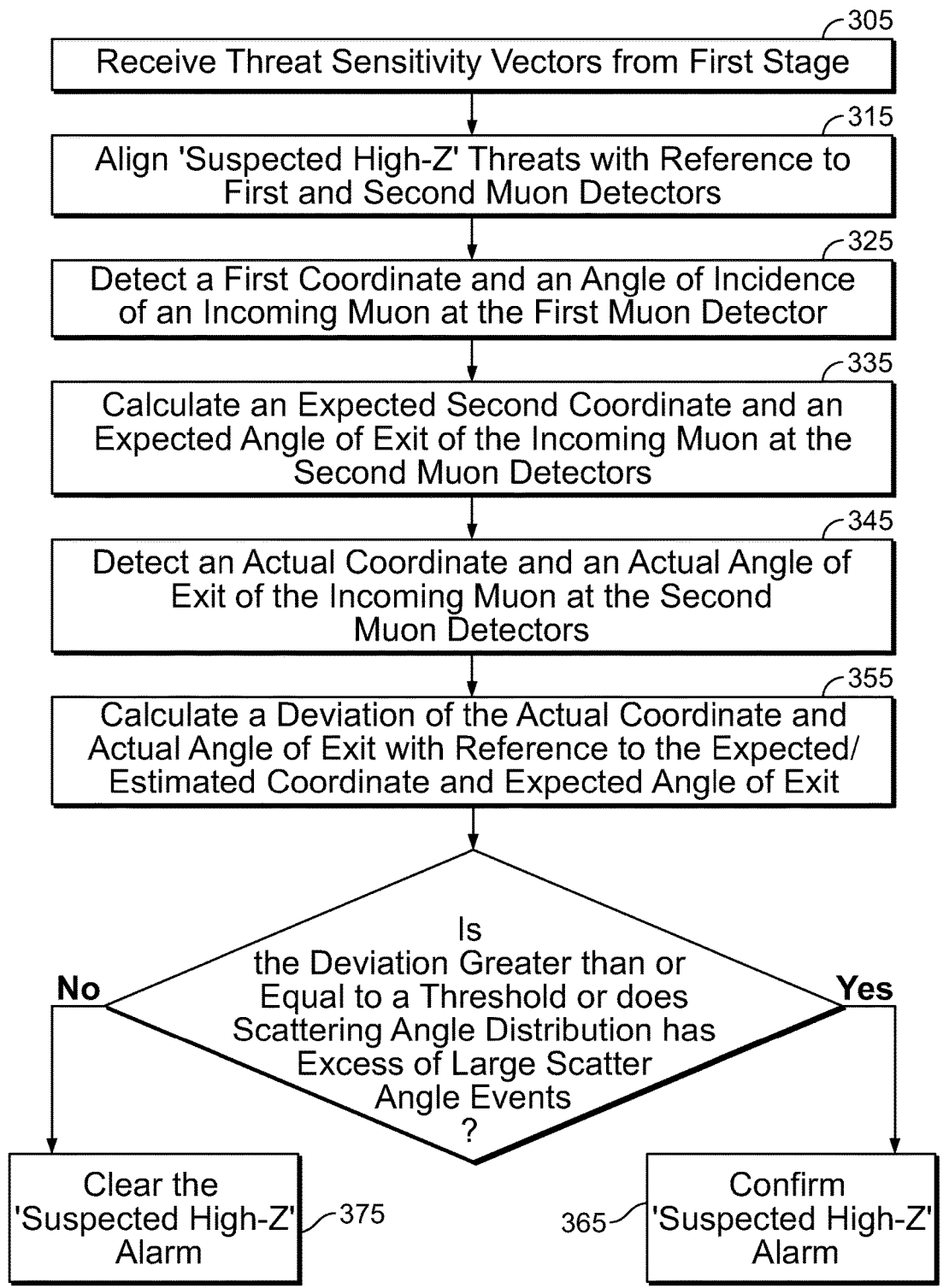
FIG. 3 is a flow chart illustrating a plurality of exemplary steps of a threat alarm resolution method in accordance with an embodiment.

A plurality of methods can be used to derive threat alarms from the muon measurements. FIG. 3 is a flow chart illustrating a plurality of exemplary steps of a threat alarm resolution method, in accordance with an embodiment, implemented by at least one processor in data communication with a first stage threat detection system and a second stage muon threat alarm resolution system. At step 305, a plurality of threat sensitivity vectors, with reference to a cargo under inspection, are received from the first stage threat detection system. The plurality of threat sensitivity vectors comprise data such as, but not limited to, a) number of 'suspected high-Z' objects/threats in the cargo, b) a plurality of 'suspected high-Z' parameters such as position/location, suspected area/volume, shape, size and c) a plurality of cargo content parameters such as dimensions, density and approximate density and Z distribution of the cargo content in the vicinity of the 'suspected high-Z' areas/objects. The plurality of threat sensitivity vectors are utilized, at step 315, to align the 'suspected high-Z' threat areas (within the cargo) with reference to a first and second muon detectors placed above and below the cargo, respectively, in the second stage muon threat alarm resolution system.

Thereafter, at step 325, a first coordinate and an angle of incidence of an incoming muon are detected at the first muon detectors. At step 335, the first coordinate and angle of incidence are used to calculate an expected/estimated second coordinate and an expected/estimated angle of exit of the incoming muon at the second muon detectors. In one embodiment, a momentum of the incoming muon is used as a filter to improve an accuracy of the expected/estimated second coordinate and angle of exit of the incoming muon. Next, an actual coordinate and an actual angle of exit of the incoming muon are detected at the second muon detectors, at step 345. Now, at step 355, a deviation (that is, an angle of deflection/scatter) of the actual coordinate and actual angle of exit with reference to the expected/estimated coordinate and expected angle of exit is calculated. In accordance with an embodiment, a statistical distribution of the deviations for a plurality of incoming muons is determined (also referred to as 'deviation distribution'). It should be appreciated that alternate embodiments use reconstruction algorithms such as point of closest approach (POCA) or expectation maximization (EM) to determine the point(s) of muon interaction within the cargo and angle(s) of deflection/scatter (that is, the deviation of the actual angle of exit with reference to the expected/estimated angle of exit of the muons).

In another embodiment, apart from performing steps 315 to 355 corresponding to 'suspected high-Z threat' areas (within the cargo), steps 315 to 355 are repeated for at least one second location (different from the 'suspected high-Z threat' areas) where there is cargo similar (in terms of density and Z distribution) to the cargo around the 'suspected high-Z' threat but without the threat. In other words, step 315 is repeated to have the at least one second location aligned with reference to the first and second muon detectors. Thereafter, steps 325 to 355 are also repeated to generate muon information corresponding to the second location. In this embodiment, the muon information (that is, a first coordinate and an angle of incidence of an incoming muon at the first muon detectors and an actual coordinate and an actual angle of exit of the incoming muon at the second muon detectors) at the second location, without the threat, is used to compensate for cargo scattering.

At step 365, if the deviation (or the statistical distribution thereof) is greater than or equal to a predetermined threshold then the 'suspected high-Z' threat is confirmed. On the other hand, if the deviation (or the statistical distribution thereof) is below the predetermined threshold then, at step 375, the 'suspected high-Z' threat is cleared. In an alternate embodiment, if the deviation or a distribution of the angles of deflection/scatter has an excess of large angle scattering events, then the 'suspected high-Z' threat is confirmed.

Figure 4:
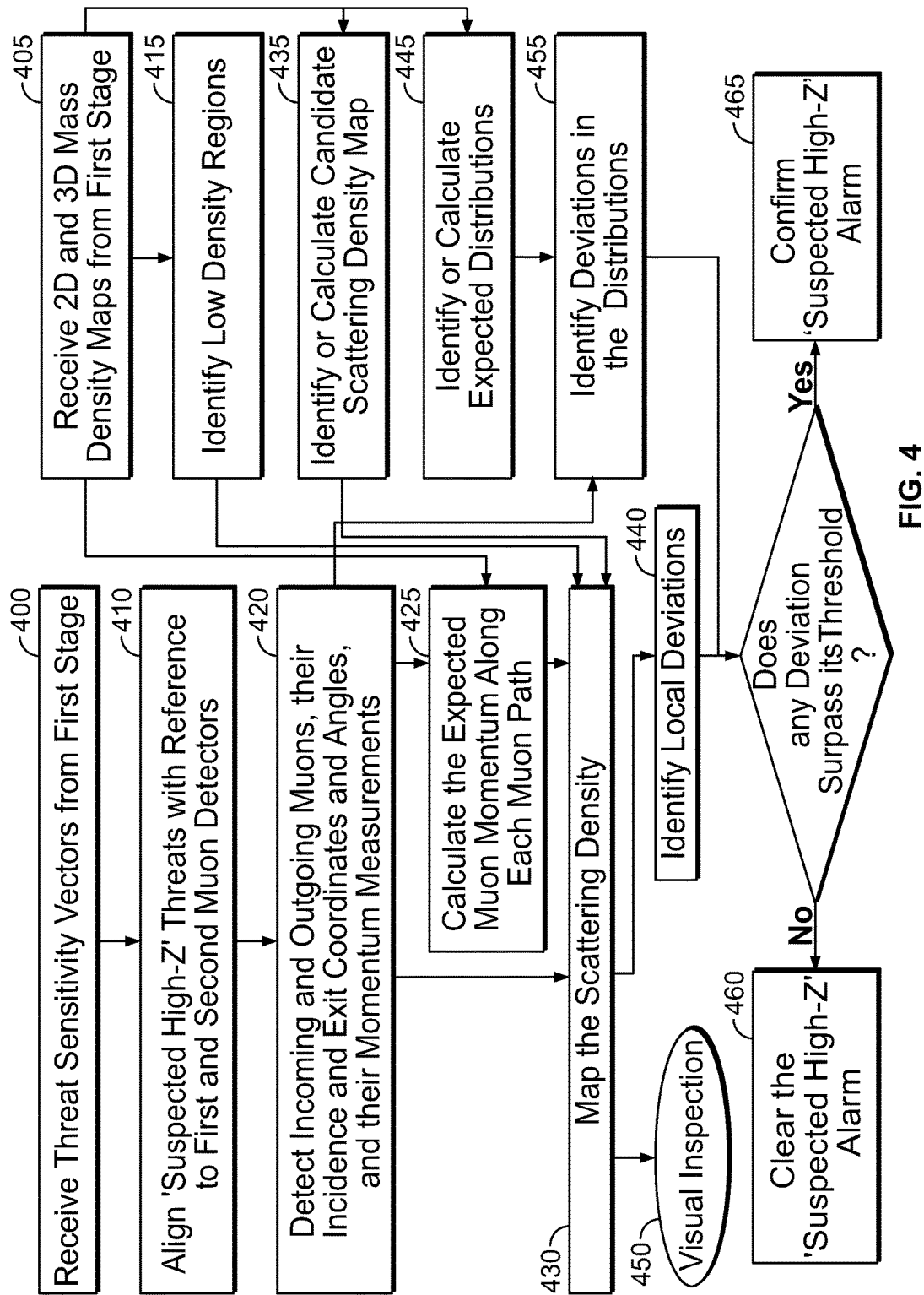
FIG. 4 is a flow chart illustrating a plurality of exemplary steps of a threat alarm resolution method, in accordance with another embodiment.

FIG. 4 is a flow chart illustrating a plurality of exemplary steps of a threat alarm resolution method, in accordance with various other embodiments, implemented by at least one processor in data communication with the first stage threat detection system and the second stage muon threat alarm resolution system. As in the method of FIG. 3, a plurality of threat sensitivity vectors are obtained from the first stage threat detection system, at step 400. At step 410, the threat sensitivity vectors are advantageously utilized to align the muon detectors with reference to the suspected high-Z threats, in the second stage muon threat alarm resolution system. Thereafter, at step 420 the locations/coordinates and directions of the muons are recorded upon entering and leaving a scanned volume, along with any measurements of the muon momentum.

In one embodiment, aimed at detecting compact threats, a 3D scattering density map is reconstructed at step 430, wherein scattering density is defined as the mean square scattering expected for muons of some nominal momentum per unit depth. In a preferred embodiment, the 3D scattering density map is binned uniformly in each dimension, yielding 3D "voxels", each with its own (average) scattering density. In some cases a 2D scattering density map is preferred, which is then built up of 2D pixels. A simplified statistical model of cosmic muons and their interaction with the materials within the scanned volume is used to find the most likely scattering density map (also known as the solution of maximal likelihood). However the model used in prior art may be too simplistic for "medium-heavy cargo", which both makes the solution of the simplified model less useful and makes it harder to converge to this solution. Also, a typical cargo slows down a muon by 0.5-1.5 GeV, depending on the content of the cargo in the suspected region identified by the first stage.

Therefore, the present invention utilizes 2D and/or 3D mass density maps obtained, at step 405, from the first stage threat detection system. The average mass density and the average scattering density can vary independently. Thus the measured mass-density cannot be used as direct indication of the scattering-density. From the mass density maps obtained at step 405 and the muon momentum measurements obtained at step 420, the expected energy loss of the muon is calculated as the muon traverses the scanned volume. At step 425, the expected energy loss is then used to calculate the expected muon momentum at each point along its path/trajectory. The expected muon momentum is thereafter incorporated in the statistical model which is used to reconstruct the scattering density map at step 430.

Another utilization of the mass density map (obtained at step 405) is at step 415 to identify regions where the mass density is particularly low, e.g. similar to that of air. This implies that the scattering density in such identified regions is also particularly low, and this information is then incorporated in the statistical model used to find the scattering density map at step 430. Such scenarios of particularly low mass density are common in medium-heavy cargo which is often packed at the bottom of the cargo, leaving the top of the scanned volume empty.

Yet another utilization of the mass density map (obtained at step 405) is at step 435 to identify a candidate scattering density map, which serves as a starting seed for reconstructing/solving the statistical inference model/problem of step 430. An identified starting seed reduces computing time and increases the reliability of converging to a correct statistical inference solution. It is also advantageous to reframe the statistical inference problem in terms of deviations from, or ratio to, the candidate scattering density map. A preferred approach to identification of the candidate scattering density map is via a database of cargos whose mass and scattering densities have been measured in controlled conditions. Alternatively, the candidate scattering density map can be calculated from the mass density map.

As the location of threat is not expected to align with the voxels, a threat will typically increase the densities measured in several adjacent voxels. Such local deviations can be identified, at step 440, by summing up and filtering adjacent voxels. Both the scattering density map and these local deviations are then inspected visually, at step 450, and an alarm is automatically raised at step 465 based on the statistical significance of the local deviations or, possibly in cooperation with the operator, the cargo is cleared at step 460 in case the local deviations are found to be statistically insignificant.

The mass density maps obtained at step 405 can also be used independently of any mapping. In one embodiment a distribution of an observable, such as the scattering angle or the number of outgoing muons (from step 420), is tracked for a specific class of muons, for example those with a low scattering deflection (from step 420), and compared to a reference distribution. The reference distribution is derived, at step 445, from a database using the measured mass density map to identify similar cargos. At step 455, the deviations in selected distributions are quantified and used to automatically raise an alarm (at step 465) or, possibly in cooperation with the operator, to clear the cargo (at step 460).

The above examples are merely illustrative of the many applications of the system of present invention. Although only a few embodiments of the present invention have been described herein, it should be understood that the present invention might be embodied in many other specific forms without departing from the spirit or scope of the invention. Therefore, the present examples and embodiments are to be considered as illustrative and not restrictive, and the invention may be modified within the scope of the appended claims.

We claim:

1. A screening system to resolve an alarm detected in a cargo positioned within a scanning volume, wherein said screening system comprises a first muon detector, a second muon detector, a detector configured to detect muons, and, a processing unit, wherein said processing unit is configured to:
   receive a plurality of threat sensitivity vectors;
   record coordinates and directions of muons entering and leaving the scanning volume;
   record measurements of momentum of said muons;
   receive a two dimensional or three dimensional mass density map;
   use the two dimensional or three dimensional mass density map and the measurements of momentum of said muons to determine an expected energy loss of said muons as said muons traverse the scanned volume;
   use said an expected energy loss to determine an expected muon momentum at each point along its path; and
   use said expected muon momentum at each point along its path to reconstruct a 3D scattering density map.

2. The screening system of claim 1, wherein said plurality of threat sensitivity vectors are generated from a high energy X-ray cargo inspection system.

3. The screening system of claim 1, wherein said first and second muon detectors comprise Thin Gap Chamber (TGC) detectors.

4. The screening system of claim 1, wherein said first and second muon detectors comprise Thick Gas Electron Multiplier (THGEM) detectors.

5. The screening system of claim 1, wherein said plurality of threat sensitivity vectors comprise: a number of suspected high-Z threats, an approximate shape and an approximate size of said suspected high-Z threats, dimensional information, density information, approximate Z distribution of content of said cargo, and an area or a volume of suspected high-Z threats along a path length of a radiation beam employed for scanning said cargo.

6. The screening system of claim 1, further comprising a positioning system, wherein said positioning system comprises a range sensor to detect a position of the cargo relative to a center of said first and second muon detectors and an indicator to assist said cargo in attaining said position.

7. The screening of claim 6, wherein said indicator comprises at least one of a traffic light and a digital display showing a distance to stop said cargo.

8. The screening system of claim 1, wherein scattering density is defined as a mean square scattering expected for muons per unit depth.

9. The screening system of claim 1, wherein the processing unit is further configured to use the plurality of threat sensitivity vectors to align the muon detectors with reference to the suspected threat.

10. The screening system of claim 1, wherein said processing unit is further configured to identify regions where a mass density of said scanning volume is similar to air.

11. The screening system of claim 1, wherein said processing unit is further configured to use the mass density map to identify a candidate scattering density map, wherein said processing unit is configured to use the candidate scattering density map as a seed for reconstructing said 3D scattering density map.

12. The screening system of claim 11, wherein said processing unit is further configured to determine local deviations by summing up and filtering adjacent voxels.

13. The screening system of claim 12, wherein said processing unit is further configured to visually inspect the 3D scattering density map and the local deviations.

14. The screening system of claim 12, wherein said processing unit is further configured to activate an alarm based on a statistical significance of the local deviations.

15. The screening system of claim 1, further comprising at least two layers of muon detectors sized to be placed in a gap between wheels of said cargo.

16. The screening system of claim 1, wherein said second muon detector has a different size than said first muon detector.

17. The screening system of claim 1, wherein said first and second muon detectors comprise at least two layers of detectors that are substantially parallel.

18. The screening system of claim 17, wherein said at least two layers of first and second muon detectors are spaced at a distance ranging from approximately 50 mm to 500 mm.

19. The screening system of claim 1, wherein said first and second muon detectors have dimensions within a range of approximately 2 m×3 m (length) to 3 m×4 m (width).

20. The screening system of claim 1, wherein said first and second muon detectors have dimensions within a range of approximately 3 m×4 m (length) to 3 m×4 m (width).

* * * * *